(12) United States Patent
Hartung et al.

(10) Patent No.: US 8,481,539 B2
(45) Date of Patent: Jul. 9, 2013

(54) ALKYNYLARYL COMPOUNDS AND SALTS THEREOF, PHARMACEUTICAL COMPOSITIONS COMPRISING SAME, METHODS OF PREPARING SAME AND USES OF SAME

(75) Inventors: Ingo Hartung, Erkrath (DE); Hans Briem, Berlin (DE); Georg Kettschau, Berlin (DE); Karl-Heinz Thierauch, Berlin (DE); Ulf Bömer, Glienicke/Nordbahn (DE)

(73) Assignee: Bayer Intellectual Property GmbH, Monheim (DE)

( * ) Notice: Subject to any disclaimer, the term of this patent is extended or adjusted under 35 U.S.C. 154(b) by 166 days.

(21) Appl. No.: 12/747,880

(22) PCT Filed: Dec. 4, 2008

(86) PCT No.: PCT/EP2008/010284
§ 371 (c)(1),
(2), (4) Date: Jun. 11, 2010

(87) PCT Pub. No.: WO2009/074260
PCT Pub. Date: Jun. 18, 2009

(65) Prior Publication Data
US 2010/0261730 A1 Oct. 14, 2010

(30) Foreign Application Priority Data
Dec. 11, 2007 (EP) .................................... 07076073

(51) Int. Cl.
| | | |
|---|---|---|
| *A01N 43/58* | (2006.01) | |
| *A01N 43/60* | (2006.01) | |
| *C07D 401/00* | (2006.01) | |
| *C07D 403/00* | (2006.01) | |
| *C07D 405/00* | (2006.01) | |
| *C07D 409/00* | (2006.01) | |
| *C07D 513/02* | (2006.01) | |
| *C07D 515/02* | (2006.01) | |
| *A61K 31/50* | (2006.01) | |
| *A61K 31/495* | (2006.01) | |

(52) U.S. Cl.
USPC .......................... 514/248; 544/238; 546/119

(58) Field of Classification Search
USPC ........................... 514/248; 544/238; 546/119
See application file for complete search history.

(56) References Cited

U.S. PATENT DOCUMENTS
2009/0099219 A1* 4/2009 Hartung et al. ............... 514/275

* cited by examiner

*Primary Examiner* — Sreeni Padmanabhan
*Assistant Examiner* — Uma Ramachandran
(74) *Attorney, Agent, or Firm* — Thomas C. Blankinship

(57) ABSTRACT

The invention relates to alkynylaryl compounds according to the general formula (I) in which A, B, D, E, $R^a$, $R^1$, $R^3$, $R^4$, $R^5$ and q are as defined in the claims, and salts, N-oxides, solvates and prodrugs thereof, to pharmaceutical compositions comprising said alkynylaryl compounds, to methods of preparing said alkynylaryl compounds, to intermediate compounds useful in said methods, to uses of said intermediate compounds in the preparation of said alkynylaryl compounds, as well as to uses of said alkynylaryl compounds for manufacturing a pharmaceutical composition for the treatment of diseases of dysregulated vascular growth or of diseases which are accompanied with dysregulated vascular growth.

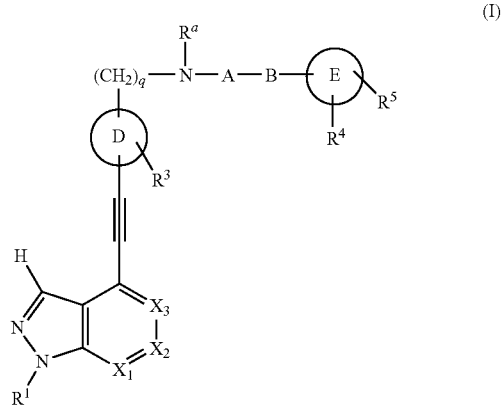

9 Claims, No Drawings

ALKYNYLARYL COMPOUNDS AND SALTS THEREOF, PHARMACEUTICAL COMPOSITIONS COMPRISING SAME, METHODS OF PREPARING SAME AND USES OF SAME

The present invention relates to alkynylaryl compounds of general formula (I) and salts, N-oxides, solvates and prodrugs thereof, to pharmaceutical compositions comprising said alkynylaryl compounds, to methods of preparing said alkynylaryl compounds, to intermediate compounds useful in said methods, to uses of said intermediate compounds in the preparation of said alkynylaryl compounds, as well as to uses of said alkynylaryl compounds.

Dysregulated vascular growth plays a critical role in a variety of inflammatory diseases, in particular psoriasis, delayed type hypersensitivity, contact dermatitis, asthma, multiple sclerosis, restenosis, rheumatoid arthritis and inflammatory bowl disease. Aberrant vascular growth is also involved in neovascular ocular diseases such as age-related macular degeneration and diabetic retinopathy. Additionally, sustained vascular growth is accepted as one hallmark of cancer development (Hanahan, D.; Weinberg, R. A. Cell 2000, 100, 57). While tumors initially grow either as an avascular mass or by co-opting existing host vessels, growth beyond a few $mm^3$ in size is depending on the induction of vessel neogrowth in order to sufficiently provide the tumor with oxygen and nutrients. Induction of angiogenesis is a prerequisite that the tumor surpasses a certain size (the so called angiogenic switch). An intricate signaling interaction network between cancer cells and the tumor microenvironment triggers the induction of vessel growth from existing vasculature. The dependence of tumors on neovascularization has led to a new treatment paradigm in cancer therapy (Ferrara et al. Nature 2005, 438, 967; Carmeliet Nature 2005, 438, 932). Blocking tumor neovascularization by small molecule or antibody-mediated inhibition of relevant signal transduction pathways holds a great promise for extending currently available therapy options.

The development of the cardiovascular system involves two basic stages. In the initial vasculogenesis stage, which only occurs during embryonal development, angioblasts differentiate into endothelial cells which subsequently form a primitive vessel network. The subsequent stage, termed angiogenesis, involves the remodeling of the initial vasculature and sprouting of new vessels (Risau, W. Nature 1997, 386, 671; Jain, R. K. Nat. Med. 2003, 9, 685). Physiologically, angiogenesis occurs in wound healing, muscle growth, the female cycle and in the above mentioned disease states.

It has been found that receptor tyrosine kinases of the vascular endothelial growth factor (VEGF) family (VEGFRs), the platelet-derived growth factor receptors (PDGFRs) and the Tie2 (tyrosine kinase with immunoglobulin and epidermal growth factor homology domain) receptor tyrosine kinase are essential for both developmental and disease-associated angiogenesis (Judah Folkman Nat. Rev. Drug Disc. 2007, 6, 273; Ferrara et al Nat. Med. 2003, 9, 669; Rakesh K. Jain Nat. Med. 2003, 9, 685; Dumont et al. Genes Dev. 1994, 8, 1897; Sato et al. Nature 1995, 376, 70).

Inhibition of VEGFR signaling has been recently validated as an anti-angiogenic treatment paradigm by the approval of VEGFR signaling inhibitors such as Nexavar® for the treatment of renal cell carcinoma and VEGF antibodies for the treatment of colorectal cancer (Avastin®) or age-related macular degeneration (Macugen®).

As angiogenesis is a complex process combining various functional processes, regulation of angiogenesis depends on multiple signaling pathways. Combined inhibition of more than one pathway of relevance for angiogenesis would therefore be expected to increase anti-angiogenic efficacy. On the other hand, antiangiogenic therapy in cancerous and even more so in non-cancerous diseases is expected to require the inhibition of angiogenic processes for an extended time, for example by continuos treatment of patients with an anti-angiogenic drug ("chronic therapy"). In order to allow for use in continuos dosing regimens for the treatment of cancerous diseases and even more so for the treatment of non-cancerous diseases an anti-angiogenic agent would require to be active and selective for the inhibition of angiogenic processes thereby reducing the likelihood of adverse side effects.

Pyrazolopyridines have been disclosed as antimicrobiotic substances (e.g. Attaby et al., Phosphorus, Sulfur and Silicon and the related Elements 1999, 149, 49-64; Goda et al. Bioorg. Med. Chem. 2004, 12, 1845). U.S. Pat. No. 5,478,830 further discloses fused heterocycles for the treatment of atherosclerosis. Pyrazolopyridines have also been described as PDE4-Inhibitors (WO2006004188, US20060004003).

A single 3-amino-1H-pyrazolo[3,4-b]pyridine with modest EGFR inhibitory activity has been published by Cavasotto et al. (Bioorg. Med. Chem. Lett. 2006, 16, 1969). 5-aryl-1H-3-aminopyrazolo[3,4-b]pyridines have been reported as GSK-3 inhibitors (Witherington et al. Bioorg. Med. Chem. Lett. 2003, 13, 1577). WO 2003068773 discloses 3-aminopyrazolopyridine derivatives as GSK-3 inhibitors.

WO 2004113304 discloses 3-amino-indazoles as inhibitors of protein tyrosine kinases, particularly as inhibitors as VEGFR2 kinase. WO 2006050109, WO 2006077319 and WO 2006077168 disclose 3-aminopyrazolopyridines as tyrosine kinase inhibitors.

WO 2002024679 discloses tetrahydropyridine-substituted pyrazolopyridines as IKK inhibitors. WO 2004076450 further discloses 5-heteroaryl-pyrazolopyridines as p38 inhibitors. US 20040192653 and US 20040176325 inter alia disclose 4-H-pyrazolopyridines as p38 inhibitors. WO 2005044181 discloses pyrazolopyridines as Abl kinase inhibitors.

There is a great need for a receptor tyrosine kinase inhibitor which shows balanced inhibition of VEGFR2 signaling and in addition inhibition of PDGFRβ and/or Tie2 signaling while being selective against those tyrosine kinases whose functional role are primarily relevant for non-angiogenic processes, such as, for example TrkA and/or the insulin receptor kinase (InsR).

Inhibition of InsR kinase for example is known to cause diabetic phenotypes and disadvantageous effects on the liver. The insulin/IGF-1 receptor inhibitor NVP-ADW742 for example at concentrations which inhibit both the insulin and IGF-1 receptors strongly potentiated desoxycholic acid-induced apoptotic cell death, which as a consequence predicts strong liver toxic effects in case of impaired bile flow (Dent et al. Biochem. Pharmacol. 2005, 70, 1685). Even worse, inhibition of the neuronal insulin receptor causes Alzheimer-like disturbances in oxidative/energy brain metabolism (Hoyer et al. Ann. N.Y. Acad. Sci. 1999, 893, 301). The nerve growth factor/TrkA signaling system is known to be important for neuronal systems by modulating the growth, differentiation and survival of central and peripheral neurons (Distefano et al. Annu. Rep. Med. Chem. 1993, 28, 11).

It was now found that compounds of the present invention not only display potent activity as inhibitors of VEGFR2 kinase activity but also a favorable selectivity profile within the class of receptor tyrosine kinase with potent co-inhibition of PDGFRβ and/or Tie2 while being selective against other tyrosine kinases, such as the insulin receptor kinase or TrkA.

Preferred compounds of the present invention show balanced inhibition of VEGFR2 and PDGFRβ and Tie2 while being >100 fold less active against InsR and TrkA.

The solution to the above-mentioned novel technical problem is achieved by providing compounds derived, in accordance with the present invention, from a class of alkynylaryl compounds and salts, N-oxides, solvates and prodrugs thereof, methods of preparing alkynylaryl compounds, a pharmaceutical composition containing said alkynylaryls, use of said alkynylaryl compounds and a method for treating diseases with said alkynylaryl compounds, all in accordance with the description, as defined in the claims of the present application.

The compounds of Formula (I) below, salts, N-oxides, solvates and prodrugs thereof are collectively referred to as the "compounds of the present invention". The invention thus relates to compounds of general formula (I):

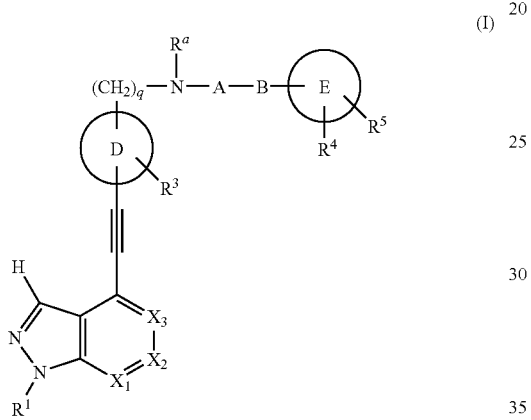

in which:
- $R^1$ represents H or —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;
- $R^2$ represents hydrogen, halogen, cyano, —NR$^{d1}$R$^{d2}$, —OR$^c$, —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, heteroaryl, wherein said residues are unsubstituted or one or more times substituted independently from each other with $R^7$;
- $R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;
- $R^4$, $R^5$, $R^6$, $R^7$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, NR$^{d1}$R$^{d2}$, and —OP(O)(OR$^c$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;
- $R^8$ is selected from the group comprising, preferably consisting of, $C_1$-$C_6$-alkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, —NR$^{d1}$R$^{d2}$, and —OP(O)(OR$^c$)$_2$;
- $R^a$ is selected from the group comprising, preferably consisting of, hydrogen and $C_1$-$C_6$-alkyl;
- $R^b$ is selected from the group comprising, preferably consisting of, hydroxyl, —OR$^c$, —SR$^c$, —NR$^{d1}$R$^{d2}$, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;
- $R^c$ is selected from the group comprising, preferably consisting of, hydrogen, —C(O)$R^e$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —OR$^f$, —NR$^{d1}$R$^{d2}$, or —OP(O)(OR$^f$)$_2$;
- $R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —C(O)$R^e$, —S(O)$_2$$R^e$, or —C(O)NR$^{g1}$R$^{g2}$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)$R^e$, —S(O)$_2$$R^e$, or —OP(O)(OR$^f$)$_2$; or
- $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, halogen, —NR$^{g1}$R$^{g2}$, —OR$^f$, —C(O)$R^e$, —S(O)$_2$$R^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, and/or —S(O)$_2$— group, and can optionally contain one or more double bonds
- $R^{d3}$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;
- $R^e$ is selected from the group comprising, preferably consisting of, —NR$^{g1}$R$^{g2}$, $C_1$-$C_6$-alkyl, $C_3$-$C_6$-cycloalkyl, $C_1$-$C_6$-alkoxy, aryl and heteroaryl;
- $R^f$ is selected from the group comprising, preferably consisting of, hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —NR$^{g1}$R$^{g2}$;
- $R^{g1}$R$^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl;
- $R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$- alkoxy, halogen or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, and/or —S(O)$_2$— group, and can optionally contain one or more double bonds;

A is selected from the group comprising, preferably consisting of, —C(O)—, —C(S)—, —C(=NR$^a$)—, —C(O)NR$^a$—, —C(=NR$^a$)NR$^a$—, —S(O)$_2$—, —S(O)(=NR$^a$)—, —S(=NR$^a$)$_2$—, —C(S)NR$^a$—, —C(O)C(O)—, —C(O)C(O)NR$^a$—, —C(O)NR$^a$C(O)—, —C(S)NR$^a$C(O)—, and —C(O)NR$^a$C(S)—;

B is a bond or selected from the group comprising, preferably consisting of C$_1$-C$_6$-alkylene, C$_3$-C$_{10}$-cycloalkylene, and C$_3$-C$_{10}$-heterocycloalkylene;

D, E are, independently from each other, arylene or heteroarylene;

$X_1$, $X_2$, $X_3$ are, independently from each other, a CH or CR$^2$ or a nitrogen atom;

zero, one or two of $X_1$, $X_2$, $X_3$ being nitrogen; and q represents an integer of 0, 1, or 2;

or a salt, an N-oxide, a solvate or a prodrug thereof, wherein, when one or more of R$^a$, R$^b$, R$^c$, R$^{d1}$, R$^{d2}$, R$^{d3}$, R$^e$, R$^f$, R$^{g1}$, R$^{g2}$, or R$^8$ is (are) present in one position in the molecule as well as in one or more further positions in the molecule, said R$^a$, R$^b$, R$^c$, R$^{d1}$, R$^{d2}$, R$^{d3}$, R$^e$, R$^f$, R$^{g1}$, R$^{g2}$, or R$^8$ has (have), independently from each other, the same meanings as defined above in said first position in the molecule and in said second or further positions in the molecule, it being possible for the two or more occurrences of R$^a$, R$^b$, R$^c$, R$^{d1}$, R$^{d2}$, R$^{d3}$, R$^e$, R$^f$, R$^{g1}$, R$^{g2}$, or R$^8$ within a single molecule to be identical or different. For example, when R$^a$ is present twice in the molecule, then the meaning of the first R$^a$ may be H, for example, and the meaning of the second R$^a$ may be methyl, for example.

In accordance with a preferred embodiment, the present invention relates to compounds of formula (I), supra, in which:

R$^1$ represents H or —C(O)R$^b$, or is selected from the group comprising, preferably consisting of, C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, wherein said residues are unsubstituted or substituted one or more times, independently from each other, with R$^6$;

R$^2$ represents hydrogen, halogen, cyano, NR$^{d1}$R$^{d2}$, —OR$^c$, —C(O)R$^b$, or is selected from the group comprising, preferably consisting of, C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, aryl, heteroaryl, wherein said residues are unsubstituted or one or more times substituted independently from each other with R$^7$;

R$^3$ is selected from the group comprising, preferably consisting of, hydrogen, C$_1$-C$_6$-alkyl, C$_1$-C$_6$-alkoxy, C$_1$-C$_6$-haloalkyl, C$_1$-C$_6$-haloalkoxy, hydroxy, amino, halogen, and cyano;

R$^4$, R$^5$, R$^6$, R$^7$ independently from each other, are selected from the group comprising, preferably consisting of, hydrogen, C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, and —OP(O)(OR$^c$)$_2$, wherein C$_1$-C$_6$-alkyl, aryl, heteroaryl, C$_3$-C$_{10}$-heterocycloalkyl and C$_3$-C$_{10}$-cycloalkyl are optionally substituted one or more times by R$^8$;

R$^8$ is selected from the group comprising, preferably consisting of, C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, and —OP(O)(OR$^c$)$_2$;

R$^a$ is selected from the group comprising, preferably consisting of, hydrogen and C$_1$-C$_6$-alkyl;

R$^b$ is selected from the group comprising, preferably consisting of, hydroxyl, —OR$^c$, —SR$^c$, —NR$^{d1}$R$^{d2}$, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^c$ is selected from the group comprising, preferably consisting of, hydrogen, —C(O)R$^e$, C$_1$-C$_6$-alkyl, C$_1$-C$_6$-haloalkyl C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, aryl, —OR$^f$, —NR$^{d1}$R$^{d2}$, or —OP(O)(OR$^f$)$_2$;

R$^{d1}$, R$^{d2}$ independently from each other are selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, or for a group —C(O)R$^e$, —S(O)$_2$R$^e$, or —C(O)NR$^{g1}$R$^{g2}$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, halogen, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, and/or —S(O)$_2$— group, and can optionally contain one or more double bonds R$^{d3}$ is selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl, wherein C$_1$-C$_6$-alkyl, and C$_3$-C$_{10}$-cycloalkyl are optionally substituted one or more times with C$_1$-C$_6$-alkyl, C$_3$-C$_{10}$-cycloalkyl, hydroxyl, halogen, C$_1$-C$_6$-haloalkyl or C$_1$-C$_6$-alkoxy;

R$^e$ is selected from the group comprising, preferably consisting of, —NR$^{g1}$R$^{g2}$, C$_1$-C$_6$-alkyl, C$_3$-C$_6$-cycloalkyl, C$_1$-C$_6$-alkoxy, aryl and heteroaryl;

R$^f$ is selected from the group comprising, preferably consisting of, hydrogen, —C(O)R$^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —NR$^{g1}$R$^{g2}$;

R$^{g1}$, R$^{g2}$ independently from each other are selected from the group comprising, preferably consisting of hydrogen, C$_1$-C$_6$-alkyl, C$_3$-C$_{10}$-cycloalkyl, C$_3$-C$_{10}$-heterocycloalkyl, aryl, and heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —$S(O)_2$— group, and can optionally contain one or more double bonds;

A is selected from the group comprising, preferably consisting of, —C(O)—, and —C(O)$NR^a$—;

B is a bond or selected from the group comprising, preferably consisting of $C_1$-$C_3$-alkylene, and $C_3$-$C_6$-cycloalkylene;

D, E are, independently from each other, arylene or heteroarylene;

$X_1$, $X_2$, $X_3$ are, independently from each other, a CH or $CR^2$ or a nitrogen atom;

zero, one or two of $X_1$, $X_2$, $X_3$ being nitrogen; and q represents an integer of 0, 1, or 2;

or a salt, an N-oxide, a solvate or a prodrug thereof, wherein, when one or more of $R^a$, $R^b$, $R^c$, $R^{d1}$, $R^{d2}$, $R^{d3}$, $R^e$, $R^f$, $R^{g1}$, $R^{g2}$, or $R^8$ is (are) present in one position in the molecule as well as in one or more further positions in the molecule, said $R^a$, $R^b$, $R^c$, $R^{d1}$, $R^{d2}$, $R^{d3}$, $R^e$, $R^f$, $R^{g1}$, $R^{g2}$, or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^{d3}$, $R^e$, $R^f$, $R^{g1}$, $R^{g2}$, or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a more preferred embodiment, the present invention relates to compounds of formula (I), supra, in which:

$R^1$ represents H or —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ represents hydrogen, halogen, cyano, $NR^{d1}R^{d2}$, —$OR^c$, —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, heteroaryl, wherein said residues are unsubstituted or one or more times substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$, $R^5$, $R^6$, $R^7$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —$S(O)_2R^b$, —$OR^c$, —$NR^{d1}R^{d2}$, and —OP(O)($OR^c$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;

$R^8$ is selected from the group comprising, preferably consisting of, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —$S(O)_2R^b$, —$OR^c$, —$NR^{d1}R^{d2}$, and —OP(O)($OR^c$)$_2$;

$R^a$ is selected from the group comprising, preferably consisting of, hydrogen and $C_1$-$C_6$-alkyl;

$R^b$ is selected from the group comprising, preferably consisting of, hydroxyl, —$OR^c$, —$SR^c$, —$NR^{d1}R^{d2}$, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^c$ is selected from the group comprising, preferably consisting of, hydrogen, —C(O)$R^e$, $C_1$-$C_6$-alkyl, $C_1$-$C_6$-haloalkyl $C_3$-$C_{10}$-cycloalkyl, $C_3$-$C_{10}$-heterocycloalkyl, alkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —$OR^f$, —$NR^{d1}R^{d2}$, or —OP(O)($OR^f$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —C(O)$R^e$, —$S(O)_2R^e$, or —C(O)$NR^{g1}R^{g2}$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$NR^{g1}R^{g2}$, —$OR^f$, —C(O)$R^e$, —$S(O)_2R^e$, or —OP(O)($OR^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, halogen, —$NR^{g1}R^{g2}$, —$OR^f$, —C(O)$R^e$, —$S(O)_2R^e$, or —OP(O)($OR^f$)$_2$; whereby the carbon backbone of this heterocycloalkyl ring can optionally be interrupted one or more times, the same way or differently, by a member of the group comprising, preferably consisting of, NH, $NR^{d3}$, oxygen or sulphur, and can optionally be interrupted one or more times, the same way or differently, with a —C(O)—, —S(O)—, and/or —$S(O)_2$— group, and can optionally contain one or more double bonds $R^{d3}$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;

$R^e$ is selected from the group comprising, preferably consisting of, —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group comprising, preferably consisting of, hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, $C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

A is selected from the group comprising, preferably consisting of, —C(O)—, and —C(O)$NR^a$—;

B is a bond or selected from the group comprising, preferably consisting of $C_1$-$C_3$-alkylene, and $C_3$-$C_6$-cycloalkylene;

D is phenylene;

E is arylene or heteroarylene;

$X_1$, $X_2$, $X_3$ are, independently from each other, a CH or $CR^2$ or a nitrogen atom;

zero, one or two of $X_1$, $X_2$, $X_3$ being nitrogen, and q represents an integer of 0, 1, or 2;

or a salt, an N-oxide, a solvate or a prodrug thereof, wherein, when one or more of $R^a$, $R^b$, $R^c$, $R^{d1}$, $R^{d2}$, $R^{d3}$, $R^e$, $R^f$, $R^{g1}$, $R^{g2}$, or $R^8$ is (are) present in one position in the molecule as well as in one or more further positions in the molecule, said $R^a$, $R^b$, $R^c$, $R^{d1}$, $R^{d2}$, $R^{d3}$, $R^e$, $R^f$, $R^{g1}$, $R^{g2}$, or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^{d3}$, $R^e$, $R^f$, $R^{g1}$, $R^{g2}$, or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a more particularly preferred embodiment, the present invention relates to compounds of formula (I), supra, in which:

$R^1$ represents $C_1$-$C_6$-alkyl;

$R^3$ is selected from the group comprising, preferably consisting of, hydrogen, $C_1$-$C_6$-alkyl, and halogen;

$R^4$, $R^5$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$^2R^b$, —$OR^c$, —$NR^{d1}R^{d2}$, and —OP(O)(O$R^b$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;

$R^8$ is selected from the group comprising, preferably consisting of, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —$OR^c$, —$NR^{d1}R^{d2}$, and —OP(O)(O$R^c$)$_2$;

$R^a$ is hydrogen;

$R^b$ is selected from the group comprising, preferably consisting of, hydroxyl, —$OR^c$, —$SR^c$, —$NR^{d1}R^{d2}$, $C_1$-$C_6$-alkyl, and $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^c$ is selected from the group comprising, preferably consisting of, hydrogen, —C(O)$R^e$, $C_1$-$C_6$-alkyl, $C_1$-$C_6$-haloalkyl $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —$OR^f$, —$NR^{d1}R^{d2}$, or —OP(O)(O$R^f$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, or for a group —C(O)$R^e$, —S(O)$_2R^e$, or —C(O)$NR^{g1}R^{g2}$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —$NR^{g1}R^{g2}$, —$OR^f$, —C(O)$R^e$, —S(O)$_2R^e$, or —OP(O)(O$R^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, halogen, —$NR^{g1}R^{g2}$, —$OR^f$, —C(O)$R^e$, —S(O)$_2R^e$, or —OP(O)(O$R^f$)$_2$; whereby the carbon backbone of this heterocycloalkyl ring can optionally be interrupted one or more times, the same way or differently, by a member of the group comprising, preferably consisting of, NH, $NR^{d3}$, oxygen or sulphur, and can optionally be interrupted one or more times, the same way or differently, with a —C(O)—, —S(O)—, and/or —S(O)$_2$— group, and can optionally contain one or more double bonds $R^{d3}$ is selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;

$R^e$ is selected from the group comprising, preferably consisting of, —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is selected from the group comprising, preferably consisting of, hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, and heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, and/or —S(O)$_2$— group, and can optionally contain one or more double bonds;

A is selected from the group comprising, preferably consisting of, —C(O)—, and —C(O)$NR^a$—;

B is a bond or selected from the group comprising, preferably consisting of $C_1$-$C_3$-alkylene, and $C_3$-$C_6$-cycloalkylene;

D is phenylene;

E is arylene or heteroarylene;

$X_1$ is a CH group;

$X_2$ is a nitrogen atom; and $X_3$ is a CH group; and q represents an integer of 0, 1, or 2;

or a salt, an N-oxide, a solvate or a prodrug thereof, wherein, when one or more of $R^a$, $R^b$, $R^c$, $R^{d1}$, $R^{d2}$, $R^{d3}$, $R^e$, $R^f$, $R^{g1}$, $R^{g2}$, or $R^8$ is (are) present in one position in the molecule as well as in one or more further positions in the molecule, said $R^a$, $R^b$, $R^c$, $R^{d1}$, $R^{d2}$, $R^{d3}$, $R^e$, $R^f$, $R^{g1}$, $R^{g2}$, or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$, $R^{d3}$, $R^e$, $R^f$, $R^{g1}$, $R^{g2}$, or $R^8$ within a single molecule to be identical or different. For example, when $R^a$ is present twice in the molecule, then the meaning of the first $R^a$ may be H, for example, and the meaning of the second $R^a$ may be methyl, for example.

Within the context of the present application, the terms as mentioned in this description and in the claims have preferably the following meanings:

The term "alkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and isomers thereof.

The term "haloalkyl" is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and isomers thereof.

The term "haloalkoxy" is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "cycloalkyl" is to be understood as preferably meaning a $C_3$-$C_{10}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cycloalkyl group to the rest of the molecule can be provided to the double or single bond; and also as meaning such a saturated or unsaturated cycloalkyl group being optionally substituted one or more times, independently from each other, with a $C_1$-$C_6$ alkyl group and/or a halogen and/or an $OR^f$ group and/or a $NR^{g1}R^{g2}$ group; such as, for example, a 2-methyl-cyclopropyl group, a 2,2-dimethylcyclopropyl group, a 2,2-dimethylcyclobutyl group, a 3-hydroxycyclopentyl group, a 3-hydroxycyclohexyl group, a 3-dimethylaminocyclobutyl group, a 3-dimethylaminocyclopentyl group or a 4-dimethylaminocyclohexyl group.

The term "heterocycloalkyl" is to be understood as preferably meaning a $C_3$-$C_{10}$ cycloalkyl group, as defined supra, featuring the indicated number of ring atoms, wherein one or more ring atom(s) is (are) (a) heteroatom(s) such as NH, $NR^{d3}$, O, S, or (a) group(s) such as a C(O), S(O), $S(O)_2$, or, otherwise stated, in a $C_n$-cycloalkyl group, (wherein n is an integer of 3, 4, 5, 6, 7, 8, 9, or 10), one or more carbon atom(s) is (are) replaced by said heteroatom(s) or said group(s) to give such a $C_n$ cycloheteroalkyl group; and also as meaning an unsaturated heterocycloalkyl group containing one or more double bonds in the C-backbone, wherein the linkage of said heterocyclolalkyl group to the rest of the molecule can be provided to the double or single bond; and also as meaning such a saturated or unsaturated heterocycloalkyl group being optionally substituted one or more times, independently from each other, with a $C_1$-$C_6$ alkyl group and/or a halogen and/or an $OR^f$ group and/or a $NR^{g1}R^{g2}$ group. Thus, said $C_n$ cycloheteroalkyl group refers, for example, to a three-membered heterocycloalkyl, expressed as $C_3$-heterocycloalkyl, such as oxiranyl ($C_3$). Other examples of heterocycloalkyls are oxetanyl ($C_4$), aziridinyl ($C_3$), azetidinyl ($C_4$), tetrahydrofuranyl ($C_5$), pyrrolidinyl ($C_5$), morpholinyl ($C_6$), dithianyl ($C_6$), thiomorpholinyl ($C_6$), piperidinyl ($C_6$), tetrahydropyranyl ($C_6$), piperazinyl ($C_6$), trithianyl ($C_6$), homomorpholinyl ($C_7$), homopiperazinyl ($C_7$) and chinuclidinyl ($C_8$); said cycloheteroalkyl group refers also to, for example, 4-methylpiperazinyl, 3-methyl-4-methylpiperazine, 3-fluoro-4-methylpiperazine, 4-dimethylaminopiperidinyl, 4-methylaminopiperidinyl, 4-aminopiperidinyl, 3-dimethylaminopiperidinyl, 3-methylaminopiperidinyl, 3-aminopiperidinyl, 4-hydroxypiperidinyl, 3-hydroxypiperidinyl, 2-hydroxypiperidinyl, 4-methylpiperidinyl, 3-methylpiperidinyl, 3-dimethylaminopyrrolidinyl, 3-methylaminopyrrolidinyl, 3-aminopyrrolidinyl or methylmorpholinyl.

The term "halogen" or "Hal" is to be understood as preferably meaning fluorine, chlorine, bromine, or iodine.

The term "alkenyl" is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group, and isomers thereof.

The term "alkynyl" is to be understood as preferably meaning branched and unbranched alkynyl, e.g. an ethynyl, prop-1-yn-1-yl, but-1-yn-1-yl, but-2-yn-1-yl, or but-3-yn-1-yl group, and isomers thereof.

As used herein, the term "aryl" is defined in each case as having 3-12 carbon atoms, preferably 6-12 carbon atoms, such as, for example, cyclopropenyl, phenyl, tropyl, indenyl, naphthyl, azulenyl, biphenyl, fluorenyl, anthracenyl etc, phenyl being preferred.

As used herein, the term "heteroaryl" is understood as meaning an aromatic ring system which comprises 3-16 ring atoms, preferably 5 or 6 or 9 or 10 atoms, and which contains at least one heteroatom which may be identical or different, said heteroatom being such as nitrogen, NH, $NR^{d3}$, oxygen, or sulphur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H- pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

The term "alkylene", as used herein in the context of the compounds of general formula (I) is to be understood as meaning an optionally substituted alkyl chain or "tether", having 1, 2, 3, 4, 5, or 6 carbon atoms, i.e. an optionally substituted —CH$_2$— ("methylene" or "single membered tether" or e.g. —C(Me)$_2$-), —CH$_2$—CH$_2$— ("ethylene", "dimethylene", or "two-membered tether"), —CH$_2$—CH$_2$—CH$_2$— ("propylene", "trimethylene", or "three-membered tether"), —CH$_2$—CH$_2$—CH$_2$—CH$_2$— ("butylene", "tetramethylene", or "four-membered tether"), —CH$_2$—CH$_2$—CH$_2$—CH$_2$—CH$_2$— ("pentylene", "pentamethylene" or "five-membered ether"), or —CH$_2$—CH$_2$—CH$_2$—CH$_2$—CH$_2$—CH$_2$— ("hexylene", "hexamethylene", or six-membered tether") group. Preferably, said alkylene tether is 1, 2, 3, 4, or 5 carbon atoms, more preferably 1 or 2 carbon atoms.

The term "cycloalkylene", as used herein in the context of the compounds of general formula (I) is to be understood as meaning an optionally substituted cycloalkyl ring, having 3, 4, 5, 6, 7, 8, 9 or 10, preferably 3, 4, 5, or 6, carbon atoms, i.e. an optionally substituted cyclopropyl, cyclobutyl, cyclopenyl, cyclohexyl, cycloheptyl, cyclooctyl, cyclononyl, or cyclodecyl ring, preferably a cyclopropyl, cyclobutyl, cyclopentyl or cyclohexyl ring.

The term "heterocycloalkylene", as used herein in the context of the compounds of general formula (I) is to be understood as meaning a cycloalkylene ring, as defined supra, but which contains at least one heteroatom which may be identical or different, said heteroatom being such as NH, NR$^{d3}$, oxygen or sulphur.

The term "arylene", as used herein in the context of the compounds of general formula (I) is to be understood as meaning an optionally substituted monocyclic or polycyclic arylene aromatic system e.g. arylene, naphthylene and biarylene, preferably an optionally substituted phenyl ring or "tether", having 6 or 10 carbon atoms. More preferably, said arylene tether is a ring having 6 carbon atoms, i.e. a "phenylene" ring. If the term "arylene" or e.g. "phenylene" is used it is to be understood that the linking residues can be arranged to each other in ortho-, para- and meta-position, eg. an optionally substituted moiety of structure:

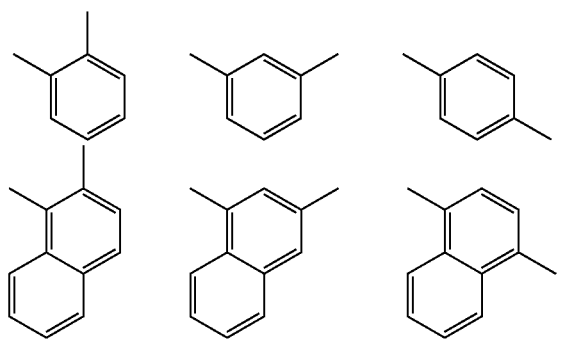

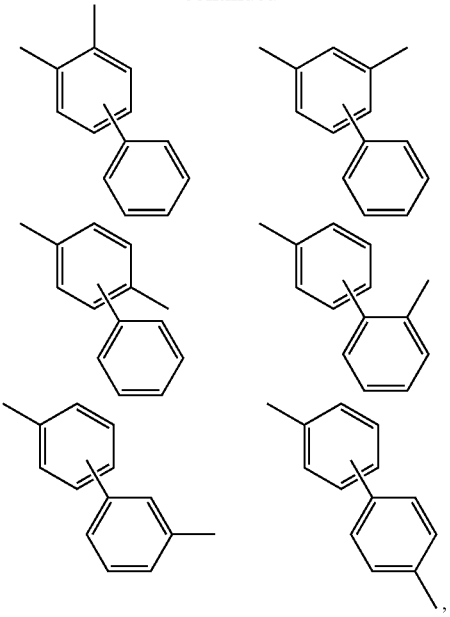

in which linking positions on the rings are shown as non-attached bonds.

The term "heteroarylene", as used herein in the context of the compounds of general formula (I) is to be understood as meaning an optionally substituted monocyclic or polycyclic heteroarylene aromatic system, e.g. heteroarylene, benzoheteroarylene, preferably an optionally substituted 5-membered heterocycle, such as, for example, furan, pyrrole, pyrazole, thiazole, oxazole, isoxazole, or thiophene or "tether", or a 6-membered heterocycle, such as, for example, pyridine, pyrimidine, pyrazine, pyridazine. More preferably, said heteroarylene tether is a ring having 6 carbon atoms, e.g. an optionally substituted structure as shown supra for the arylene moieties, but which contains at least one heteroatom which may be identical or different, said heteroatom being such as nitrogen, NH, NR$^{d3}$, oxygen, or sulphur. If the term "heteroarylene" is used it is to be understood that the linking residues can be arranged to each other in ortho-, para- and meta-position.

As used herein, the term "C$_1$-C$_6$", as used throughout this text, e.g. in the context of the definition of "C$_1$-C$_6$-alkyl", or "C1-C$_6$-alkoxy", is to be understood as meaning an alkyl group having a finite number of carbon atoms of 1 to 6, i.e. 1, 2, 3, 4, 5, or 6 carbon atoms. It is to be understood further that said term "C$_1$-C$_6$" is to be interpreted as any sub-range comprised therein, e.g. C$_1$-C$_6$, C$_2$-C$_5$, C$_3$-C$_4$, C$_1$-C$_2$, C$_1$-C$_3$, C$_1$-C$_4$, C$_1$-C$_5$, C$_1$-C$_6$; preferably C$_1$-C$_2$, C$_1$-C$_3$, C$_1$-C$_4$, C$_1$-C$_5$, C$_1$-C$_6$; more preferably C$_1$-C$_4$.

Similarly, as used herein, the term "C$_2$-C$_6$", as used throughout this text, e.g. in the context of the definitions of "C$_2$-C$_6$-alkenyl" and "C$_2$-C$_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "C$_2$-C$_6$" is to be interpreted as any sub-range comprised therein, e.g. C$_2$-C$_6$, C$_3$-C$_5$, C$_3$-C$_4$, C$_2$-C$_3$, C$_2$-C$_4$, C$_2$-C$_5$; preferably C$_2$-C$_3$.

As used herein, the term "C$_3$-C$_{10}$", as used throughout this text, e.g. in the context of the definitions of "C$_3$-C$_{10}$-cycloalkyl" or "C$_3$-C$_{10}$-heterocycloalkyl", is to be understood as meaning a cycloalkyl group having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; preferably $C_3$-$C_6$.

As used herein, the term "$C_3$-$C_6$", as used throughout this text, e.g. in the context of the definitions of "$C_3$-$C_6$-cycloalkyl" or "$C_3$-$C_6$-heterocycloalkyl", is to be understood as meaning a cycloalkyl group having a finite number of carbon atoms of 3 to 6, i.e. 3, 4, 5, or 6 carbon atoms. It is to be understood further that said term "$C_3$-$C_6$" is to be interpreted as any sub-range comprised therein, e.g. $C_3$-$C_4$, $C_4$-$C_6$, $C_5$-$C_6$.

As used herein, the term "$C_6$-$C_{11}$", as used throughout this text, e.g. in the context of the definitions of "$C_6$-$C_{11}$-aryl", is to be understood as meaning an aryl group having a finite number of carbon atoms of 5 to 11, i.e. 5, 6, 7, 8, 9, 10 or 11 carbon atoms, preferably 5, 6, or 10 carbon atoms. It is to be understood further that said term "$C_6$-$C_{11}$" is to be interpreted as any sub-range comprised therein, e.g. $C_5$-$C_{10}$, $C_6$-$C_9$, $C_7$-$C_8$; preferably $C_5$-$C_6$.

As used herein, the term "$C_5$-$C_{10}$", as used throughout this text, e.g. in the context of the definitions of "$C_5$-$C_{10}$-heteroaryl", is to be understood as meaning a heteroaryl group having a finite number of carbon atoms of 5 to 10, in addition to the one or more heteroatoms present in the ring i.e. 5, 6, 7, 8, 9, or 10 carbon atoms, preferably 5, 6, or 10 carbon atoms. It is to be understood further that said term "$C_5$-$C_{10}$" is to be interpreted as any sub-range comprised therein, e.g. $C_6$-$C_9$, $C_7$-$C_8$, $C_7$-$C_8$; preferably $C_5$-$C_6$.

As used herein, the term "$C_1$-$C_3$", as used throughout this text, e.g. in the context of the definitions of "$C_1$-$C_3$-alkylene", is to be understood as meaning an alkylene group as defined supra having a finite number of carbon atoms of 1 to 3, i.e. 1, 2, or 3. It is to be understood further that said term "C1-C3" is to be interpreted as any sub-range comprised therein, e.g. $C_1$-$C_2$, or $C_2$-$C_3$.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

In "stereoisomers", the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers.

In order to limit different types of isomers from each other reference is made to IUPAC Rules Section E (Pure Appl Chem 45, 11-30, 1976).

The compounds of the present invention according to Formula (I) can exist in free form or in a salt form. A suitable pharmaceutically acceptable salt of the alkynylaryl compounds of the present invention may be, for example, an acid-addition salt of an alkynylaryl compound of the invention which is sufficiently basic, for example, an acid-addition salt with, for example, an inorganic or organic acid, for example hydrochloric, hydrobromic, sulphuric, phosphoric, trifluoroacetic, para-toluenesulphonic, methylsulphonic, citric, tartaric, succinic or maleic acid. In addition, another suitable pharmaceutically acceptable salt of an alkynylaryl compound of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glutamine, ethylglutamine, lysine, 1,6-hexadiamine, ethanolamine, glucosamine, sarcosine, serinol, tris-hydroxy-methyl-aminomethane, aminopropandiol, sovak-base, 1-amino-2,3,4-butantriol.

The compounds of the present invention according to Formula (I) can exist as N-oxides which are defined in that at least one nitrogen of the compounds of the general Formula (I) may be oxidized.

The compounds of the present invention according to Formula (I) can exist as solvates, in particular as hydrates, wherein compounds of the present invention according to Formula (I) may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrates, hemi-, (semi-), mono-, sesqui-, di-, tri-, tetra-, penta- etc. solvates or hydrates are possible.

The compounds of the present invention according to Formula (I) can exist as prodrugs, e.g. as in vivo hydrolysable esters. As used herein, the term "in vivo hydrolysable ester" is understood as meaning an in vivo hydrolysable ester of a compound of formula (I) containing a carboxy or hydroxyl group, for example, a pharmaceutically acceptable ester which is hydrolysed in the human or animal body to produce the parent acid or alcohol. Suitable pharmaceutically acceptable esters for carboxy groups include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_{10}$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxyl group includes inorganic esters such as phosphate esters and α-acyloxyalkyl ethers and related compounds which as a result of the in vivo hydrolysis of the ester breakdown to give the parent hydroxyl group. Examples of α-acyloxyalkyl ethers include acetoxymethoxy and 2,2-dimethylpropionyloxymethoxy. A selection of in vivo hydrolysable ester forming groups for hydroxyl include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention according to Formula (I) and salts, solvates, N-oxides and prodrugs thereof may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred stereoisomers are those with the configuration which produces the more desirable biological activity. Separated, pure or partially purified configurational isomers or racemic mixtures of the compounds of this invention are also included within the scope of the present invention. The purification of said isomers and the separation of said isomeric mixtures can be accomplished by standard techniques known in the art.

Another embodiment of the present invention relates to intermediate compounds, in particular compounds of formulae 1, 3, 5 and 15. Another embodiment of the present invention relates to the use of said compounds of general formulae 1, 3, 5 and 15 for the preparation of a compound of general formula (I) as defined supra.

The compounds of the present invention can be used in treating diseases of dysregulated vascular growth or diseases which are accompanied with dysregulated vascular growth. Especially, the compounds effectively interfere with VEGFR2 and PDGFRβ and/or Tie2 signaling while showing favorable selectivity against other tyrosine kinases such as, for example, TrkA and/or the insulin receptor kinase.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

In particular, said use is in the treatment of diseases, wherein the diseases are tumors and/or metastases thereof. The compounds of the present invention can be used in particular in therapy and prevention of tumor growth and metastases, especially in solid tumors of all indications and stages with or without pre-treatment if the tumor growth is accompanied with persistent angiogenesis, principally including all solid tumors, e.g. breast, colon, renal, ovarian, prostate, thyroid, lung and/or brain tumors, melanoma, or metastases thereof.

Additionally, said use is in the treatment of chronic myelogeneous leukaemia (or "CML"), acute myelogenous leukaemia (or "AML"), acute lymphatic leukaemia, acute lymphocytic leukaemia (or "ALL"), chronic lymphocytic leukaemia, chronic lymphatic leukaemia (or "CLL") as well as other myeloid precursor hyperplasias such as polycythemia vera and myelofibrosis.

Another use is in the treatment of diseases, wherein the diseases are retinopathy, other angiogenesis dependent diseases of the eye, in particular cornea transplant rejection or age-related macular degeneration.

Yet another use is in the treatment of rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and inflammatory diseases of the bowel, such as, for example, Crohn's disease.

A further use is in the suppression of the development of atherosclerotic plaque formation and for the treatment of coronary and peripheral artery disease.

Another use is in the treatment of diseases associated with stromal proliferation or characterized by pathological stromal reactions and for the treatment of diseases associated with deposition of fibrin or extracellular matrix, such as, for example, fibrosis, cirrhosis, carpal tunnel syndrome.

Yet another use is in the treatment of gynaecological diseases where inhibition of angiogenic, inflammatory and stromal processes with pathological character can be inhibited, such as, for example, endometriosis, pre-eclampsia, postmenopausal bleeding and ovarian hyperstimulation.

Another use is in the treatment of diseases, wherein the diseases are ascites, oedema such as brain tumor associated oedema, high altitude trauma, hypoxia induced cerebral oedema, pulmonary oedema and macular oedema or oedema following burns and trauma, chronic lung disease, adult respiratory distress syndrome, bone resorption and for the treatment of benign proliferating diseases such as myoma, benign prostate hyperplasia.

A further use is in wound healing for the reduction of scar formation, and for the reduction of scar formation during regeneration of damaged nerves.

Yet another aspect of the invention is a method of treating a disease of dysregulated vascular growth or diseases which are accompanied with dysregulated vascular growth, by administering an effective amount of a compound of general formula (I) described supra.

In particular, the diseases of said method are tumors and/or metastases thereof, in particular solid tumors of all indications and stages with or without pre-treatment if the tumor growth is accompanied with persistent angiogenesis, principally including all solid tumors, e.g. breast, colon, renal, ovarian, prostate, thyroid, lung and/or brain tumors, melanoma, or metastases thereof.

Additionally, diseases of said method are chronic myelogeneous leukaemia (or "CML"), acute myelogenous leukaemia (or "AML"), acute lymphatic leukaemia, acute lymphocytic leukaemia (or "ALL"), chronic lymphocytic leukaemia, chronic lymphatic leukaemia (or "CLL") as well as other myeloid precursor hyperplasias such as polycythemia vera and myelofibrosis.

Further diseases of said method are retinopathy, other angiogenesis dependent diseases of the eye, in particular cornea transplant rejection or age-related macular degeneration.

Further diseases of said method are rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and inflammatory diseases of the bowel, such as, for example, Crohn's disease.

Further diseases of said method are the development of atherosclerotic plaques and coronary and peripheral artery diseases.

Further diseases of said method are diseases associated with stromal proliferation or characterized by pathological stromal reactions and diseases associated with deposition of fibrin or extracellular matrix, such as, for example, fibrosis, cirrhosis, carpal tunnel syndrome.

Further diseases of said method are gynaecological diseases where inhibition of angiogenic, inflammatory and stromal processes with pathological character can be inhibited, such as, for example, endometriosis, pre-eclampsia, postmenopausal bleeding and ovarian hyperstimulation.

Further diseases of said method are ascites, oedema such as brain tumor associated oedema, high altitude trauma, hypoxia induced cerebral oedema, pulmonary oedema and macular oedema or oedema following burns and trauma, chronic lung disease, adult respiratory distress syndrome, bone resorption and benign proliferating diseases such as myoma, benign prostate hyperplasia.

Another aspect of the present invention is a pharmaceutical composition which comprises a compound of general formula (I) as defined above, or as obtainable by a method described in this invention, or a pharmaceutically acceptable salt or an N-oxide or a solvate or a prodrug of said compound, and a pharmaceutically acceptable diluent or carrier, the composition being particularly suited for the treatment of diseases of dysregulated vascular growth or of diseases which are accompanied with dysregulated vascular growth as explained above.

In order to use the compounds of the present invention as pharmaceutical products, the compounds or mixtures thereof may be provided in a pharmaceutical composition, which, as well as the compounds of the present invention for enteral, oral or parenteral application contains suitable pharmaceutically acceptable organic or inorganic inert base material, e.g. purified water, gelatine, gum Arabic, lactate, starch, magnesium stearate, talcum, vegetable oils, polyalkyleneglycol, etc.

The pharmaceutical compositions of the present invention may be provided in a solid form, e.g. as tablets, dragées, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phospholipids of animal or vegetable origin, mixtures thereof and liposomes and parts thereof.

For oral application tablets, dragées or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. A dose can be administered as unit dose or in part thereof and distributed over the day. Accordingly the optimum dosage may be determined by the practitioner who is treating any particular patient.

It is possible for compounds of general formula (I) of the present invention to be used alone or, indeed in combination with one or more further drugs, particularly anti-cancer drugs or compositions thereof. Particularly, it is possible for said combination to be a single pharmaceutical composition entity, e.g. a single pharmaceutical formulation containing one or more compounds according to general formula (I) together with one or more further drugs, particularly anti-cancer drugs, or in a form, e.g. a "kit of parts", which comprises, for example, a first distinct part which contains one or more compounds according to general formula (I), and one or more further distinct parts each containing one or more further drugs, particularly anti-cancer drugs. More particularly, said first distinct part may be used concomitantly with said one or more further distinct parts, or sequentially. In addition, it is possible for compounds of general formula (I) of the present invention to be used in combination with other treatment paradigms, particularly other anti-cancer treatment paradigms, such as, for example, radiation therapy.

Another aspect of the present invention is a method which may be used for preparing the compounds according to the present invention.

The following table lists the abbreviations used in this paragraph and in the examples section as far as they are not explained within the text body. NMR peak forms are stated as they appear in the spectra, possible higher order effects have not been considered. Chemical names were generated using AutoNom2000 as implemented in MDL ISIS Draw. In some cases generally accepted names of commercially available reagents were used in place of AutoNom2000 generated names. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Flashmaster II autopurifier (Argonaut/Biotage) and eluents such as gradients of hexane/ethyl acetate or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

| Abbreviation | Meaning |
| --- | --- |
| Ac | acetyl |
| Boc | tert-butyloxycarbonyl |
| br | broad |
| CI | chemical ionisation |
| d | doublet |

| Abbreviation | Meaning |
|---|---|
| dd | doublet of doublet |
| ddd | doublet of doublet of doublet |
| dt | doublet of triplet |
| dq | doublet of quartet |
| DCM | dichloromethane |
| DIPEA | N,N-diisopropylethyl amine |
| DMF | N,N-dimethylformamide |
| DMSO | dimethyl sulfoxide |
| eq. | equivalent |
| ESI | electrospray ionisation |
| GP | general procedure |
| HPLC | high performance liquid chromatography |
| LC-MS | liquid chromatography mass spectrometry |
| m | multiplet |
| mc | centred multiplet |
| MS | mass spectrometry |
| NMR | nuclear magnetic resonance spectroscopy: chemical shifts (δ) are given in ppm. |
| Pg | protecting group |
| q | quartet |
| rf | at reflux |
| r.t. or rt | room temperature |
| s | singlet |
| sept. | septet |
| t | triplet |
| TBAF | tetra-N-butylammonium fluoride |
| TEA | triethylamine |
| TLC | thin layer chromatography |
| TFA | trifluoroacetic acid |
| THF | tetrahydrofuran |
| TMS | trimethylsilyl |
| T3P | 1-propanephosphoric acid cyclic anhydride |

The following schemes and general procedures illustrate general synthetic routes to the compounds of general formula (I) of the invention and are not intended to be limiting. It is obvious to the person skilled in the art that the order of transformations as exemplified in Schemes 1 to 11 can be modified in various ways. The order of transformations exemplified in Schemes 1 to 11 is therefore not intended to be limiting. In addition, interconversion of substituents, for example of residues $R^1$, $R^2$, $R^3$, $R^4$, $R^5$, $R^a$, $R^b$, $R^c$, $R^{d1}$, $R^{d2}$ and $R^{d3}$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999).

Scheme 1:

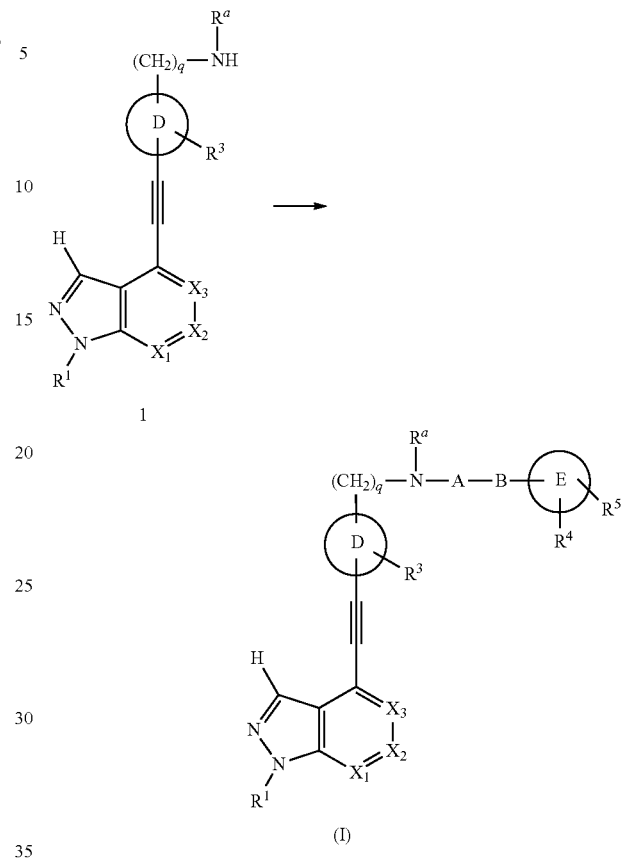

Scheme 1

General procedure for the preparation of compounds of the general formula (I) by functionalization of amines of general formula 1, wherein A, B, D, E, $R^a$, $R^1$, $R^3$, $R^4$, $R^5$, $X_1$, $X_2$, $X_3$ and q are as defined in the description and claims of this invention.

Compounds of general formula (I) can be synthesized according to the procedure depicted in Scheme 1 from amines of general formula 1 by reaction with, for example, a suitably functionalized isocyanate (leading to ureas), a suitably functionalized sulfonyl chloride (leading to sulfonyl amides) or a suitably functionalized acid chloride (leading to carboxylic amides), in the presence of a suitable base as necessary, e.g. pyridine or triethylamine, which may also be used as solvent, optionally in the presence of an inert solvent, e.g. dichloromethane, acetonitrile, DMF or THF, at temperatures ranging from −20° C. to the boiling point of the solvent, whereby room temperature is preferred.

A variety of suitable isocyanates for the above described transformation is described in the literature or commercially available. The person skilled in the art is well aware of alternative methods of forming ureas, which may be of special importance in cases were the respective isocyanates are not readily available (see Scheme 2, 3, 4 for exemplary, more specific urea-forming processes).

Processes for the preparation of functionalized (hetero)aryl sulfonyl chlorides are as well known to the person skilled in the art. Introduction of sulfonyl groups may be accomplished by sulfonylation or by oxidation of thiols. Sulfonyl chlorides may be accessible in turn from sulfonic acids by reaction with e.g. thionyl chloride, sulfuryl chloride, phosphorus pentachloride, phosphorus oxytrichloride or oxalyl chloride.

In the case of the transformation of amines of general formula 1 into amides of general formula (I) [with A being —C(O)—], it is also possible to react amines of general formula 1 with an appropriate ester according to a method described in *J. Org. Chem.* 1995, 8414 in the presence of trimethylaluminium and in suitable solvents such as toluene, at temperatures of 0° C. to the boiling point of the solvent. For amide formations, however, all processes that are known from peptide chemistry to the person skilled in the art are also available. For example, the corresponding acid, which may be obtained from the corresponding ester by saponification, can be reacted with amines of general formula 1 in aprotic polar solvents, such as, for example, DMF, via an activated acid derivative, which is obtainable, for example, with hydroxybenzotriazole and a carbodiimide, such as, for example, diisopropylcarbodiimide (DIC), at temperatures of between 0° C. and the boiling point of the solvent, preferably at 80° C., or else with preformed reagents, such as, for example, O-(7-azabenzotriazol-1-yl)-1,1,3,3-tetramethyluronium hexafluorophosphate (HATU) (see for example *Chem. Comm.* 1994, 201), at temperatures of between 0° C. and the boiling point of the solvent, preferably at room temperature, or else with activating agents such as dicyclohexylcarbodiimide (DCC)/dimethylaminopyridine (DMAP) or N-ethyl-N'-dimethylaminopropylcarbodiimide (EDCI)/dimethylaminopyridine (DMAP) or T3P (1-propanephosphoric acid cyclic anhydride). The addition of a suitable base such as, for example, N-methylmorpholine, TEA, DIPEA may be necessary. Amide formation may also be accomplished via the acid halide (which can be formed from a carboxylic acid by reaction with e.g. oxalyl chloride, thionyl chloride or sulfuryl chloride), mixed acid anhydride (which can be formed from a carboxylic acid by reaction with e.g. isobutyrochloroformiate), imidazolide (which can be formed from a carboxylic acid by reaction with e.g. carbonyldiimidazolide) or azide (which can be formed from a carboxylic acid by reaction with e.g. diphenylphosphorylazide (DPPA).

The carboxylic acids required for the above described amide coupling reactions are either commercially available or are accessible from commercially available carboxylic esters or nitriles. Alternatively, (hetero)aryls bearing a methylenenitrile substituent are easily accessible from the respective halides via a nucleophilic substitution reaction (e.g. potassium cyanide, cat. potassium iodide, ethanol/water). Incorporation of additional functionality into commercially available starting materials can be accomplished by a multitude of aromatic transformation reactions known to the person skilled in the art, including, but not limited to, electrophilic halogenations, electrophilic nitrations, Friedel-Crafts acylations, nucleophilic displacement of fluorine by oxygen or nitrogen nucleophiles, displacement reactions of benzylic halides with suitable nucleophiles and transformation of (hetero)aryl carboxylic acids into amides and subsequent reduction into benzylic amines, whereby the latter three methods are of particular relevance for the introduction of ether, amino and/or aminomethylene side chains.

Benzylic nitriles and esters (and heteroaryl analogs thereof) can be efficiently alkylated at the benzylic position under basic conditions and subsequently hydrolyzed to the corresponding alkylated acids. Conditions for ☐-alkylations of nitriles and esters include, but are not limited to, the use of alkyl bromides or alkyl iodides as electrophiles under basic conditions in the presence or absence of a phase-transfer catalyst in a mono- or biphasic solvent system. Particularly, by using excess alkyl iodides as electrophilic species α,α-dialkylated nitriles are accessible. More particularly, by using 1,☐-dihaloalkyls as electrophiles cycloalkyl moieties can be installed at the benzylic position of nitriles and esters (*J. Med. Chem.* 1975, 18, 144; WO2003022852). Even more particularly, by using a 1,2-dihaloethane, such as, for example, 1,2-dibromoethane or 1-bromo-2-chloroethane, a cyclopropane ring can be installed at the benzylic position of a nitrile or ester. The hydrolysis of nitriles to yield carboxylic acids can be accomplished, as known to the person skilled in the art, under acid or base-mediated conditions.

Scheme 2:

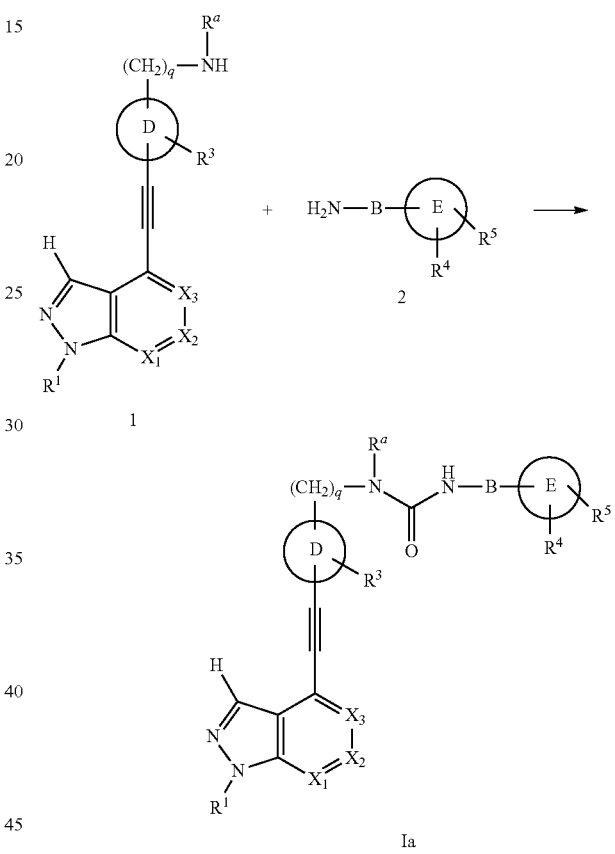

Scheme 2

More specific procedure for the preparation of compounds of the general formula Ia by reacting amines of general formula 1 with (hetero)aryl amines of general formula 2 in the presence of triphosgene, for example, wherein B, D, E, $R^a$, $R^1$, $R^3$, $R^4$, $R^5$, $X_1$, $X_2$, $X_3$ and q are as defined in the description and claims of this invention.

An alternative, more specific process of generating ureas of general formula Ia is depicted in Scheme 2. In this case, urea formation starting from amines of general formula 1 may be achieved by coupling with a second functionalized amine of general formula 2 via in situ transformation of one of the reacting amines into the respective carbamoyl chloride, aryl- or alkenylcarbamate (see for example *J. Org. Chem.* 2005, 70, 6960 and references cited therein). This process may provide an alternative to the formation and isolation of the respective isocyanate derived from one of the starting amines (see for example *Tetrahedron Lett.* 2004, 45, 4769). More particularly, ureas of formula Ia may be formed from two suitably functionalized amines and a suitable phosgene equivalent, preferably triphosgene, in an inert solvent, preferably acetonitrile, at temperatures ranging from −20° C. to the boiling point of the solvent, whereby room temperature is preferred.

Scheme 3:

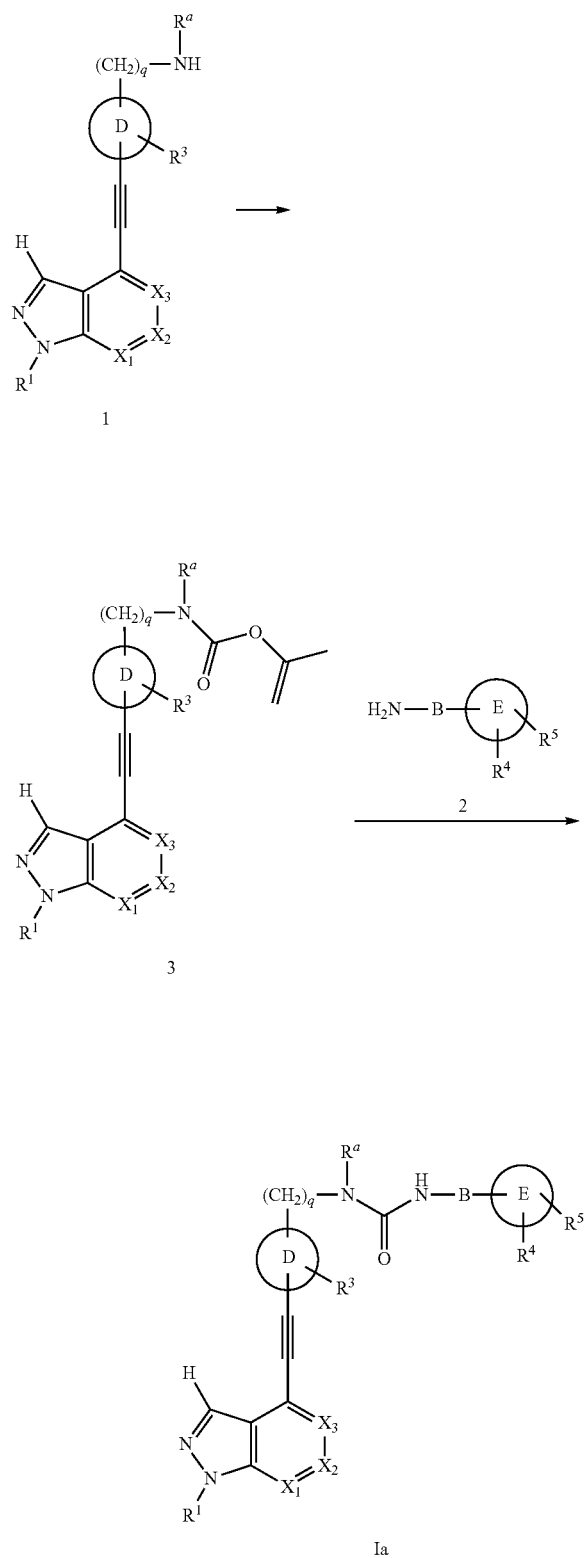

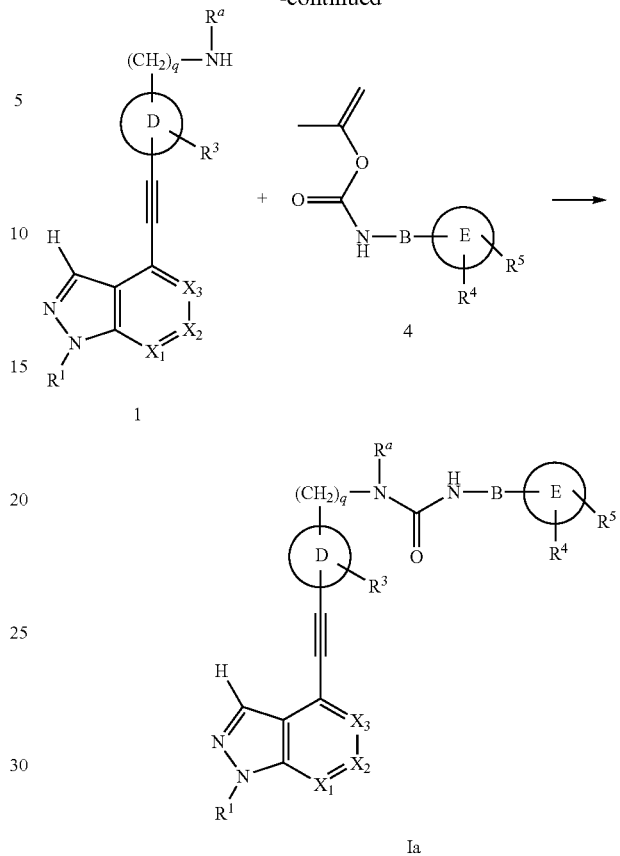

Scheme 3

Alternative more specific procedures for the preparation of compounds of the general formula Ia by either transforming amines of general formula 1 into their corresponding isopropenyl carbamates of general formula 3 and subsequent reaction with (hetero)aryl amines of general formula 2, or reacting amines of general formula 1 with isopropenyl carbamates of general formula 4, wherein B, D, E, $R^a$, $R^1$, $R^3$, $R^4$, $R^5$, $X_1$, $X_2$, $X_3$ and q are as defined in the description and claims of this invention.

The aforementioned alternative procedure for generating ureas of general formula Ia employing alkenylcarbamates, for example isopropenylcarbamates, is depicted in more detail in Scheme 3. In analogy to the aforecited publication (J. Org. Chem. 2005, 70, 6960) transformation of amines of general formula 1 into their respective isopropenyl carbamates of general formula 3 can be accomplished by reaction with isopropenyl chloro formate in the presence of an appropriate base, such as, for example, N-methylmorpholine, in a suitable solvent, such as, for example, THF. Isopropenyl carbamates of general formula 3 can then be reacted, after isolation or in situ, with (hetero)aryl amines of general formula 2 in the presence of a suitable base, such as, for example, N-methyl pyrrolidine, in a suitable solvent, such as, for example THF, to yield ureas of general formula Ia. Alternatively, (hetero)aryl amines of general formula 2 can be transformed into their corresponding isopropenyl carbamates of general formula 4 employing conditions as described above and subsequently reacted with amines of general formula 1 under conditions as described above to yield ureas of general formula Ia.

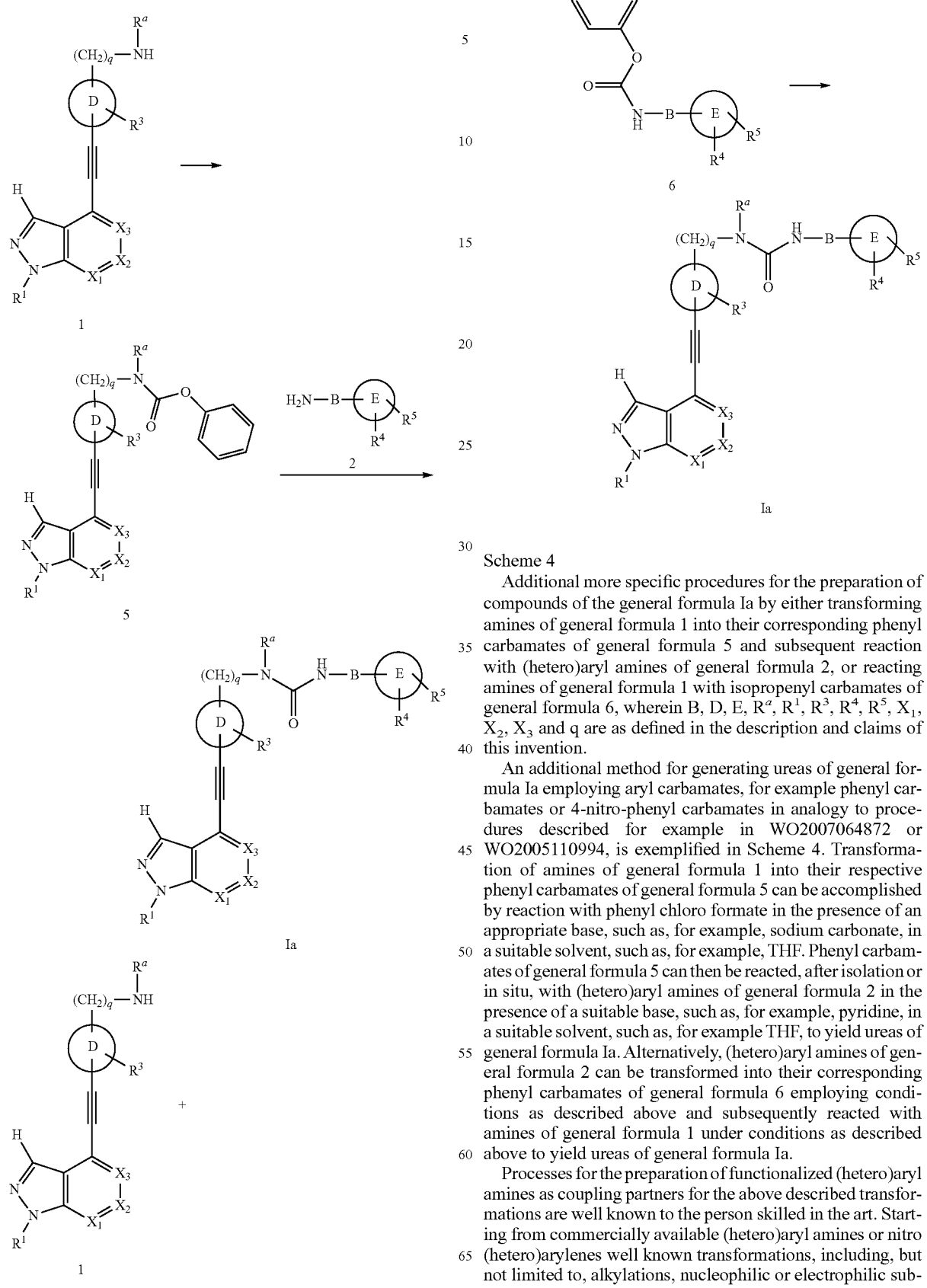

Scheme 4

Additional more specific procedures for the preparation of compounds of the general formula Ia by either transforming amines of general formula 1 into their corresponding phenyl carbamates of general formula 5 and subsequent reaction with (hetero)aryl amines of general formula 2, or reacting amines of general formula 1 with isopropenyl carbamates of general formula 6, wherein B, D, E, $R^a$, $R^1$, $R^3$, $R^4$, $R^5$, $X_1$, $X_2$, $X_3$ and q are as defined in the description and claims of this invention.

An additional method for generating ureas of general formula Ia employing aryl carbamates, for example phenyl carbamates or 4-nitro-phenyl carbamates in analogy to procedures described for example in WO2007064872 or WO2005110994, is exemplified in Scheme 4. Transformation of amines of general formula 1 into their respective phenyl carbamates of general formula 5 can be accomplished by reaction with phenyl chloro formate in the presence of an appropriate base, such as, for example, sodium carbonate, in a suitable solvent, such as, for example, THF. Phenyl carbamates of general formula 5 can then be reacted, after isolation or in situ, with (hetero)aryl amines of general formula 2 in the presence of a suitable base, such as, for example, pyridine, in a suitable solvent, such as, for example THF, to yield ureas of general formula Ia. Alternatively, (hetero)aryl amines of general formula 2 can be transformed into their corresponding phenyl carbamates of general formula 6 employing conditions as described above and subsequently reacted with amines of general formula 1 under conditions as described above to yield ureas of general formula Ia.

Processes for the preparation of functionalized (hetero)aryl amines as coupling partners for the above described transformations are well known to the person skilled in the art. Starting from commercially available (hetero)aryl amines or nitro (hetero)arylenes well known transformations, including, but not limited to, alkylations, nucleophilic or electrophilic substitutions, acylations, halogenations, nitrations, sulfonylations, (transition) metal catalyzed couplings, metallations, rearrangements, reductions, and/or oxidations may be applied to prepare functionalized amines to be used in the urea formation step. In addition to specific procedures given in the following experimental section, detailed procedures may be found in the scientific and patent literature (see for example WO2005051366, WO2005110410, WO2005113494, WO2006044823, and WO2006124462; WO2007064872 and WO2005110994).

Scheme 5:

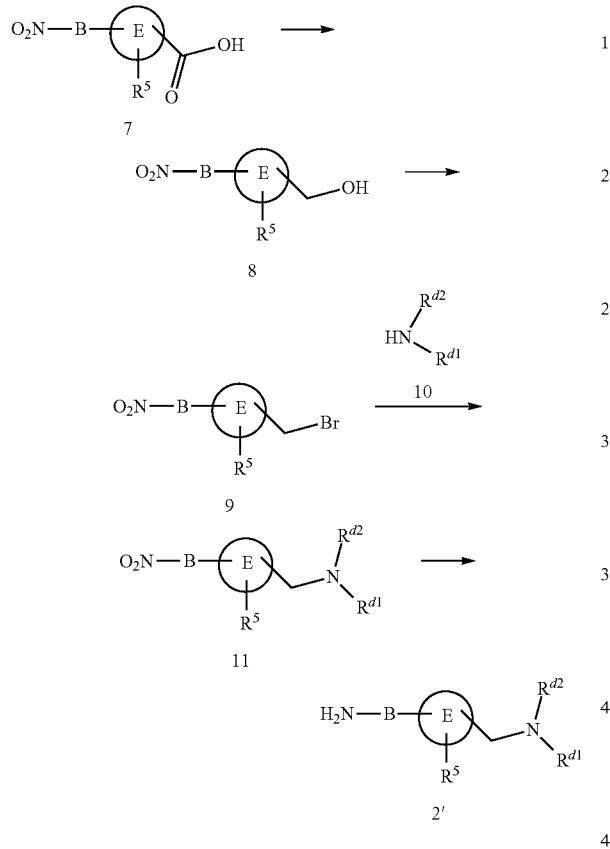

Scheme 6:

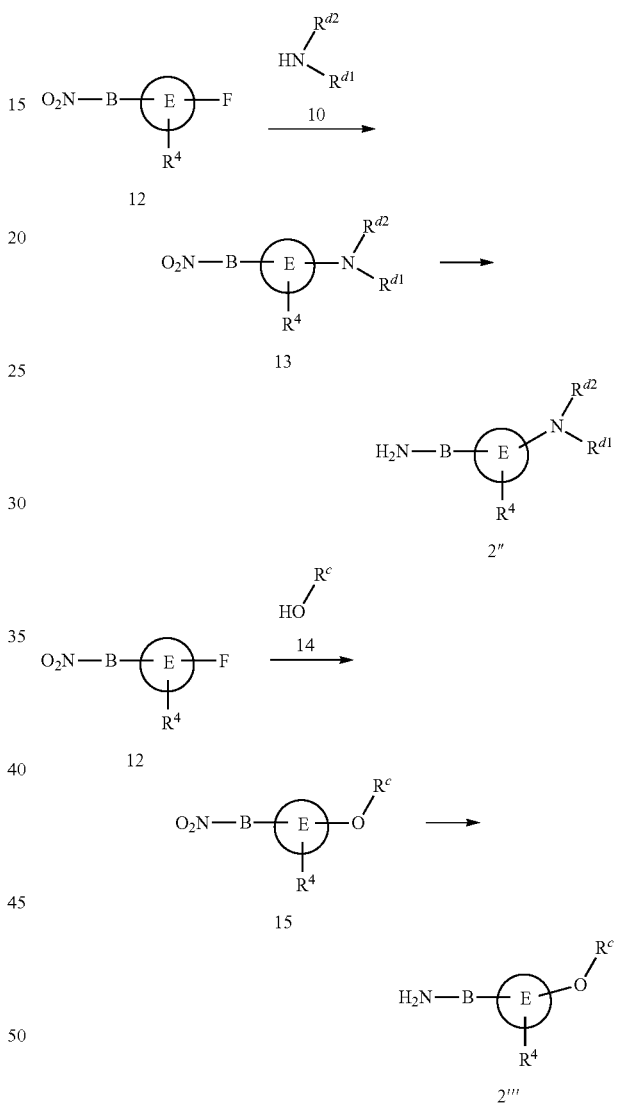

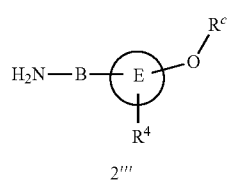

Scheme 5

Reaction sequence for the preparation of especially suitable amines of general formula 2' for urea formations according to Schemes 2, 3 and 4, in which (hetero)aryl carboxylic acids of general formula 7 are transformed into benzylic alcohols of general formula 8, then into benzylic bromides of general formula 9, then reacted with amines of general formula 10 to amines of general formula 11 and finally transformed into amines of general formula 2', wherein B, E, $R^5$, $R^{d1}$ and $R^{d2}$ are as defined in the description and claims of this invention.

A reaction sequence for the preparation of especially suitable (hetero)aryl amines for the above described urea formation processes is depicted in Scheme 5. (Hetero)aryl carboxylic acids of general formula 7 can be reduced to benzylic alcohols of general formula 8 under standard conditions as known to the person skilled in the art, for example, by reaction with borane-THF complex or sodium borohydride/iodine. Bromination of benzylic alcohols of general formula 8 leading to benzylic bromides of general formula 9 is feasible employing, for example, carbon tetrabromide in the presence of triphenylphosphine. Reaction of benzylic bromides of general formula 9 with amines of general formula 10 gives rise to benzylic amines of general formula 11 which can subsequently be reduced under standard conditions as known to the person skilled in the art, for example, by palladium-catalyzed hydrogenation or by reaction with tin (II) chloride, into amines of general formula 2'.

Scheme 6

Further reaction sequence for the preparation of especially suitable amines of general formula 2" and 2'" for urea formations according to scheme 2, in which (hetero)aryl fluorides of general formula 12 are reacted either with amines of general formula 10 or with alcohols of general formula 14 to yield after subsequent nitro reduction amines of general formula 2" or general formula 2'", respectively, wherein B, E, $R^4$, $R^c$, $R^{d1}$ and $R^{d2}$ are as defined in the description and claims of this invention.

Further reaction sequences for the preparation of especially suitable (hetero)aryl amines for the above described urea formation processes are depicted in Scheme 6. (Hetero)

aryl fluorides of general formula 12 are reacted with amines of general formula 10 in a nucleophilic aromatic substitution reaction in the presence of a suitable base, such as, for example, sodium bicarbonate, in a suitable solvent such as, for example, DMF, under heating, optionally by microwave irradiation, to form anilines of general formula 13. Alternatively, reaction with alcohols of general formula 14 in the presence of a suitable base, such as, for example, cesium carbonate, optionally under heating, gives rise to nitro ethers of general formula 15. Subsequent nitro reduction leads to amines of general formula 2" or general formula 2"', respectively.

Scheme 7:

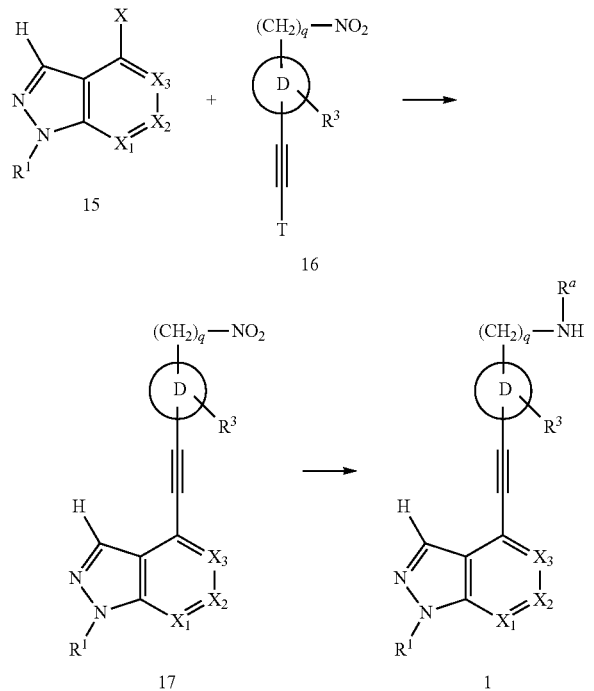

Scheme 7

General procedure for the preparation of amines of the general formula 1 by transition metal-catalyzed coupling of halides of general formula 15 with alkynes of general formula 16 and subsequent nitro reduction optionally followed by introduction of a $R^a$ group, wherein D, $R^a$, $R^1$, $R^3$, $X_1$, $X_2$, $X_3$ and q are as defined in the description and claims of this invention, T represents H or a trialkylsilyl group such as, for example, a trimethylsilyl group and X represents Cl, Br or I.

Amines of general formula 1 are accessible, for example, by transition metal-catalyzed coupling of an appropriate 4-halide of general formula 15 with terminal alkynes (with T=H) or their respective trialkylsilanes, especially their trimethyl silane derivatives (with $R=Me_3Si$), of general formula 16 followed by nitro reduction employing standard conditions as known to the person skilled in the art, such as, for example, palladium-catalyzed hydrogenation, tin (II) chloride dihydrate reduction, iron/ammonium chloride reduction, titanium (III) chloride reduction or zinc/hydrochloric acid reduction, and optionally followed by introduction of $R^a$ groups by, for example, basic alkylation or reductive alkylation (Scheme 7). More particularly, intermediates of formula 17 can be prepared starting from a halide 15 by palladium catalyzed Sonogashira-type coupling reactions with terminal alkynes (with T=H) or their respective trialkylsilanes, especially their trimethyl silane derivatives (with $R=Me_3Si$), of general formula 16. Transition metal-catalyzed couplings of (hetero)aryl halides with alkynes and trialkylsilyl alkynes are well known to the person skilled in the art (see for example (a) Chinchilla, R.; Najera, C. *Chem. Rev.* 2007, 107, 874; (b) Negishi, E.-i., Anastasia, L. *Chem. Rev.* 2003, 103, 1979; see also: (c) *Eur. J. Org. Chem.* 2005, 20, 4256; (d) *J. Org. Chem.* 2006, 71, 2535 and references therein; (e) *Chem. Commun.* 2004, 17, 1934). In the so called Sonogashira coupling, reaction of terminal alkynes (with T=H) with (hetero)aryl halides is triggered by catalytic amounts of a palladium salt in the presence of a copper salt and a base. Various palladium-catalyst/co-catalyst/ligand/base/solvent combinations have been published in the scientific literature which allow a fine-tuning of the required reaction conditions in order to allow for a broad set of additional functional groups on both coupling partners (see references in the above cited reviews). Additionally, recently developed procedures employing e.g. zinc acetylides, alkynyl magnesium salts or alkynyl trifluoroborate salts further broaden the scope of this process. Alternatively, by employing certain bases, such as, for example, tetra-N-butylammonium fluoride, trialkylsilyl-substituted alkynes such as, for example, trimethyl silyl alkynes can be coupled under Sonogashira conditions with (hetero)aryl halides.

Scheme 8:

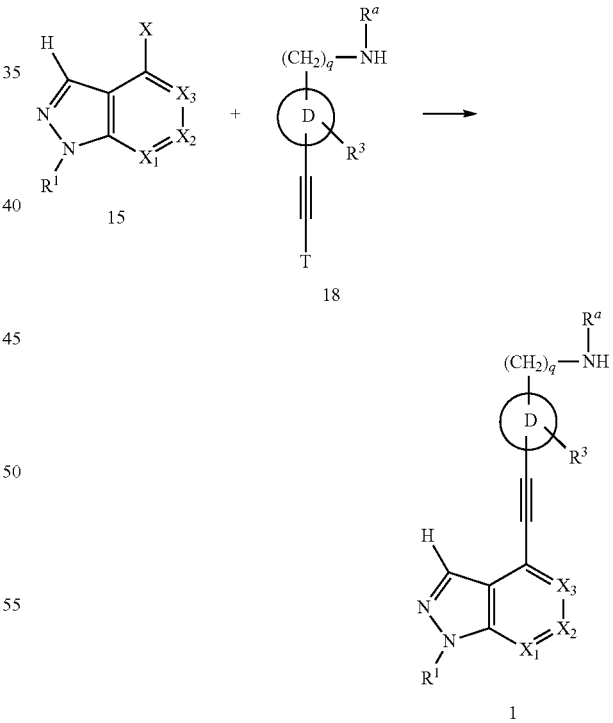

Scheme 8

Alternative general procedure for the preparation of amines of the general formula 1 by transition metal-catalyzed coupling of halides of general formula 15 with alkynes of general formula 18, wherein D, $R^a$, $R^1$, $R^3$, $X_1$, $X_2$, $X_3$ and q are as defined in the description and claims of this invention, T represents H or a trialkylsilyl group such as, for example, a trimethylsilyl group and X represents Cl, Br or I.

Alternatively, intermediates of general formula 1 are accessible by the aforementioned Sonogashira-type couplings of halides of general formula 15 with alkynes of general formula 18 under conditions as described before (Scheme 8). In some cases introduction of an amine protecting group may facilitate the coupling reaction exemplified in Scheme 8. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999).

Alkynes of general formula 16 and 18 are accessible for example from the respective nitro or amino(hetero)aryl halides by Sonogashira-type couplings with mono-protected acetylenes under conditions as described before optionally followed by cleavage of the protection group. Particularly suited mono-protected acetylenes for this process are TMS-protected acetylene and 2-methyl-but-3-yn-2-ol. Cleavage of the respective protecting group can be accomplished, for example, by treatment with tetra-N-butylammonium fluoride (TBAF) or potassium carbonate in the case of the use of TMS-acetylene, or by treatment with base in the case of the use of 2-methyl-but-3-yn-2-ol. It should be noted that, as described supra, trialkylsilyl-protected alkynes can be used directly in Sonogashira-type couplings by employing, for example, tetra-N-butylammonium fluoride (TBAF) as base. Alternatively, compounds of general formula 16 and 18 are accessible form their respective carbaldehydes by, for example, (a) Corey-Fuchs homologation (*Tetrahedron Lett.* 1972, 14, 3769), (b) reaction with TMS-diazomethane (*Chem. Comm.* 1973, 151), (c) reaction with the Gilbert-Seyferth reagent (*J. Org. Chem.* 1971, 36, 1379; *J. Org. Chem.* 1996, 61, 2540) or (d) reaction with the Ohira-Bestmann diazophosphono ester (*Synth. Commun.* 1989, 19, 561; *Synlett* 1996, 521).

Scheme 9:

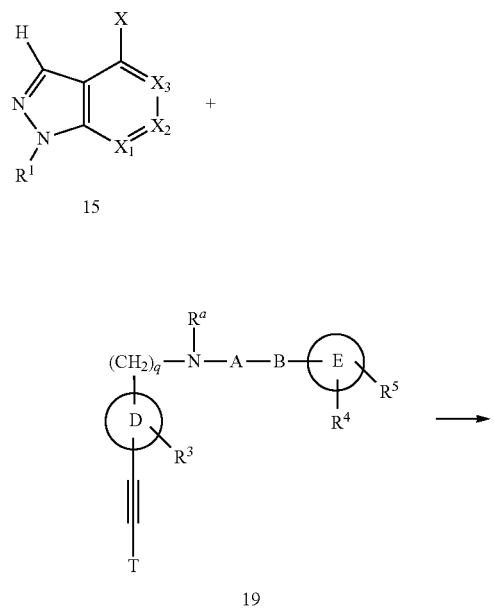

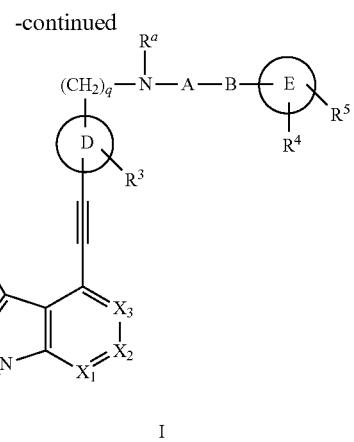

I

Scheme 9

General procedure for the preparation of compounds of the general formula (I) by transition metal-catalyzed coupling of halides of general formula 15 with alkynes of general formula 19, wherein A, B, D, E, R$^a$, R$^1$, R$^3$, R$^4$, R$^5$, X$_1$, X$_2$, X$_3$ and q are as defined in the description and claims of this invention and X represents Cl, Br or I, and T represents H or a trialkylsilyl group such as, for example, a trimethylsilyl group.

A more convergent alternative to the process exemplified before is depicted in Scheme 9, in which compounds of the present invention of general formula (I) are prepared by a transition metal catalyzed coupling of an appropriate halo precursor of general formula 15 and appropriately substituted alkynes of general formula 19. More particularly, compounds of the present invention can be prepared starting from a halide 15 by palladium-catalyzed Sonogashira-type coupling reactions with (hetero)aryl alkynes 19. Functionalized (hetero)aryl alkynes of general formula 19 can be prepared e.g. by urea formation or sulfonamide formation or amide coupling of accordingly substituted anilines (e.g. of general formula 18).

Scheme 10:

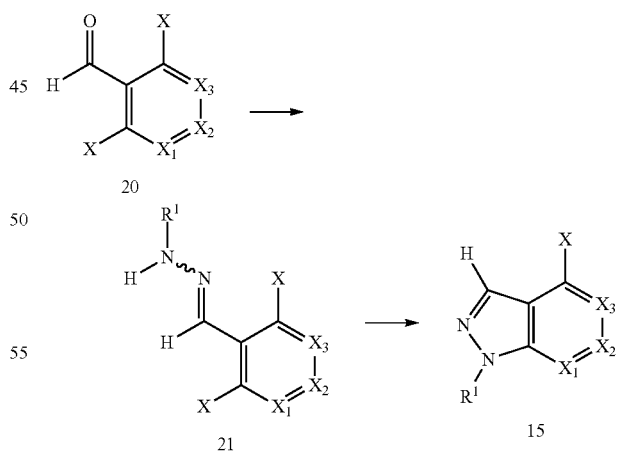

Scheme 10

General procedure for the preparation of 4-halides of the general formula 15 by transformation of carbaldehydes of general formula 20 into their respective hydrazones of general formula 21 and cyclization, wherein R$^1$, X$_1$, X$_2$ and X$_3$ are as defined in the description and claims of this invention and X represents Cl, Br or I.

Halides of general formula 15 are accessible, for example, as depicted in Scheme 10, from carbaldehydes of general formula 10 by transformation into hydrazones of formula 21 and subsequent cyclization. It is to be understood that hydrazone formation and cyclization can be accomplished in one preparative transformation or, alternatively, in two separate steps. More particularly, carbaldehydes of formula 20 can be reacted with hydrazine (e.g. hydrazine hydrate) or substituted hydrazines in an appropriate solvent, preferably in 1-propanol, at an appropriate temperature, preferably at 100 to 120° C., to yield hydrazones of formula 21 or halides of formula 15. Isolated hydrazones of formula 21 can be cyclized to halides of formula 15 e.g. by applying basic conditions, preferably by reacting with sodium hydride, in an appropriate solvent, preferably DMF, or by applying acidic conditions, e.g. by treating with, for example, TFA or acetic acid in an appropriate solvent. A variety of substituted hydrazine building blocks as required for the conversion of carbaldehydes of formula 20 into intermediates of formula 21 and/or 15 are commercially available, either in form of their free base or as various types of salts (e.g. hydrochlorides, oxalates), which can be transformed into their respective free bases by alkaline treatment either before the cyclization or in situ. Additionally, substituted alkyl-, allyl-, and benzylhydrazines (or their respective hydrochloride salts) are accessible from the respective alkyl-, allyl- and benzylhalides, preferably the respective alkyl-, allyl- and benzylbromides, by nucleophilic substitution reaction with a protected hydrazine, such as BocNHNH$_2$, in an inert solvent, preferably methanol, in the presence of an amine promoter, e.g. triethylamine, at temperatures ranging from room temperature up to the boiling point of the solvent, optionally followed by deprotection employing conditions known to the person skilled in the art, preferably, in the case of Boc deprotection, by treatment with hydrochloric acid in a mixture of diethyl ether and methanol (for a representative procedure, see *J. Med. Chem.* 2006, 49, 2170). As an alternative to the use of hydrazine hydrate in the transformation exemplified in Scheme 10, protected analogues, e.g. Boc-hydrazine (also known as tert-butyl carbazate), benzyl hydrazine or para-methoxybenzyl hydrazine can be used instead. Removal of the respective protecting group is feasible by standard transformations as known to the person skilled in the art, e.g. by hydrogenation, acid treatment or base treatment. Carbaldehydes of general formula 20 are either commercially available or can be synthesized, for example, from the respective dihalopyridines by formylation reactions, more particularly, by metallation followed by formylation of the respective metallated species (see for example *Tetrahedron Lett.* 1996, 37, 2565, U.S. Pat. No. 6,232,320 or WO 2005110410).

As stated above, the order of transformations as exemplified in previous schemes is not intended to be limiting. For example, carbaldehydes of formula 20 can also be cross-coupled with an appropriately substituted alkyne, for example of formula 16 or 18 or 19, followed by cyclization by reaction with, for example, hydrazine hydrate or a substituted hydrazine to yield compounds of formula 1 or I.

Scheme 11:

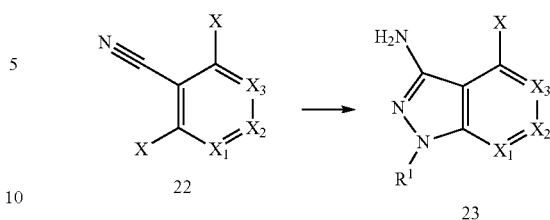

Scheme 11

General procedure for the preparation of 3-amino-4-halides of general formula 23 by transformation of (hetero)aryl nitriles of general formula 22 with hydrazine or substituted hydrazines, wherein $R^1$, $X_1$, $X_2$ and $X_3$ are as defined in the description and claims of this invention and X represents Cl, Br or I.

Alternatively, (hetero)aryl nitriles of general formula 22 can be cyclized with hydrazine (e.g. hydrazine hydrate) or substituted hydrazines to yield 3-amino-4-halides of general formula 23, which subsequently can be reacted with alkynes of general formulae 16 or 19. Desamination of the so formed intermediates, e.g. via transformation into their respective diazonium salts and subsequent acidic treatment, leads to intermediates of general formula 1 or compounds of the present invention of formula I.

General Procedures

In the subsequent paragraphs detailed general procedures for the synthesis of key intermediates and compounds of the present invention are described.

General Procedure 1 (GP 1): Hydrazone Formation

The respective heteroaryl carbaldehyde was dissolved in 1-propyl alkohol (~4-5 mL per mmol carbaldehyde), treated with the respective hydrazine (1.5-3.0 eq.) and subsequently heated to 100-120° C. in a microwave oven (Biotage Initiator®). The reaction mixture was concentrated, the residue partitioned between water and ethyl acetate, the aqueous layer reextracted with ethyl acetate, the combined organic layers dried and concentrated in vacuo to yield the desired product, which was typically used in the subsequent cyclization without further purification steps.

General Procedure 2 (GP 2): Hydrazone Cyclization

The respective hydrazone (prepared as described in GP 1) was dissolved in dry THF (~9 mL per mmol hydrazone), treated with 50-60% sodium hydride (1.2 to 2.2 eq.) and subsequently refluxed for 90 min. The reaction mixture was quenched with water, extracted with ethyl acetate, the combined organic layers dried and concentrated in vacuo. The precipitate was filtered and subsequently triturated with diisopropylether to yield the desired product. Flash column chromatography of the mother liquor provided a second batch of the analytically pure product. Alternatively, in most cases concentration of the crude reaction mixture to dryness provided the cyclized product in sufficient purity for subsequent transformations.

General Procedure 3a (GP 3a): Sonogashira Coupling (Conditions A)

One equivalent of the halopyrimidine intermediate, copper (I) iodide (0.2 eq.) and dichlorobis(triphenylphosphine)palladium (II) (Pd(PPh$_3$)$_2$Cl$_2$)(0.1 eq.) are weighed into a Schlenk flask, set under an atmosphere of argon and dissolved in dry DMF (1 mL per mmol halide). The respective ethynyl (hetero)aryl compound (1.2 eq.) and triethylamine (5-10 eq.) are added sequentially and the resulting mixture is stirred at rt (unless otherwise noted) until TLC or LCMS analysis show complete consumption of the starting halide compound. The reaction mixture is partitioned between DCM and water, the aqueous layer is extracted with DCM (3×) and the combined organic layers are dried and concentrated in vacuo. The target compound is isolated by crystallization and/or flash column chromatography and/or preparative HPLC purification.

General Procedure 3b (GP 3b): Sonogashira Coupling (Conditions B)

Dichlorobis(triphenylphosphine)palladium (II) ($PdCl_2$ $(PPh_3)_2$) (5-10 mol %) is added to a mixture of the respective halide (1 eq), copper (I) iodide (10-20 mol %), the respective alkyne (1-1.5 eq) in THF doped with triethylamine (2-10 eq). The mixture is heated to reflux in a capped flask for 18 h. After cooling to room temperature, water and ethyl acetate is added and the organic layer is separated, filtered and concentrated in vacuo and purified by HPLC.

General Procedure 3c (GP 3c): Sonogashira Coupling (Conditions C)

To a mixture of the respective halide in THF (5 mL per mmol halide) are added the alkyne (typically 1.5-2.0 eq), dichlorobis(triphenylphosphine)palladium (II) ($PdCl_2$ $(PPh_3)_2$) (5-10 mol-%), copper (I) iodide (20 mol-%), and a 1M solution of tetra-N-butylammonium fluoride in THF (2.0-3.0 eq.) under inert atmosphere at room temperature. The mixture is then allowed to react for 30 min at 80° C. in a microwave oven. After cooling to room temperature, the mixture is diluted with water, and repeatedly extracted with dichloromethane. The combined organic layers are dried over magnesium sulfate and evaporated. Column chromatography or preparative HPLC yield the pure target compound.

General Procedure 4 (GP): Desilylation of Trimethylsilyl Alkynes

To a solution of the respective (trimethylsilyl)alkyne in THF (approx. 10 mL per g alkyne) is added a 1M solution of tetra-N-butylammonium fluoride in THF (1.65 eq.), and the resulting mixture is stirred at room temperature until the reaction is completed (typically after approx. 3 h). The product is isolated by dilution with water, extraction with e.g. dichloromethane, and column chromatography (if required).

General Procedure 5 (GP 5): Urea Formation (Conditions A)

The respective (hetero)aryl amine (1 eq.) was dissolved in DCM (5-10 mL per mmol amine) and treated with the respective (commercially available) isocyanate (1-1.2 eq.). The reaction mixture was stirred at room temperature until TLC and/or LCMS indicated complete consumption of the starting aniline (usually overnight). The reaction mixture was concentrated in vacuo, the residue was taken up in ethyl acetate and water was added, the layers were separated and the aqueous layer was extracted with ethyl acetate. The combined organic layers were dried and concentrated in vacuo. The residue was optionally purified by flash column chromatography and/or trituration and/or preparative HPLC.

General Procedure 6 (GP 6): Urea Formation (Conditions B)

1.2 Eq. of a (hetero)aryl amine (usually the less functionalized one of the two amines to be coupled) were dissolved in acetonitrile (~8 mL per mmol amine), treated with triphosgene (0.4 eq.) and stirred at room temperature for 1 h upon which the second (hetero)aryl amine (usually the higher functionalized of the two amines to be coupled) was added and stirring was continued at r.t. until TLC and/or LCMS indicated complete conversion. The reaction mixture was concentrated in vacuo, the residue was taken up in ethyl acetate and water was added, the layers were separated and the aqueous layer was extracted with ethyl acetate. The combined organic layers were dried and concentrated in vacuo. The residue was optionally purified by flash column chromatography and/or trituration and/or preparative HPLC.

General Procedure 7 (GP 7): Urea Formation with Phenylcarbamates

The respective (hetero)aryl amine (1 eq.) was dissolved in THF (~10 mL per mmol amine) and treated with pyridine (40 eq.) and the respective (hetero)aryl carbamic acid phenyl ester (1 eq.; prepared from the respective (hetero)aryl amine precursor by treatment with phenyl chloroformate in analogy to procedures described in WO2007064872 or WO2005110994)). The reaction mixture was heated to 100° C. for 15 min in a Biotage Initiator microwave oven upon which LCMS analysis usually showed complete turnover (otherwise heating to 100° C. was continued until LCMS analysis showed completion of turnover). The reaction mixture was concentrated in vacuo and the residue was isolated either by trituration or by flash column chromatography or by preparative HPLC purification.

General Procedure 8 (GP 8): Formation of Isopropenyl Carbamates

In analogy to *J. Org. Chem.* 2005, 70, 6960

The respective (hetero)aryl amine (1 eq.) was dissolved in THF (~2.5 mL per mmol amine) and treated with N-methylmorpholine (1.2 eq.). The resulting solution was cooled to 4° C. and treated dropwise with chloro-isopropenyl formate (1.2 eq.). Stirring was continued at rt until TLC or LCMS analysis showed completion of turnover. The reaction mixture was quenched with water and usually extracted with ethyl acetate. The combined organic layers were dried and concentrated in vacuo. Trituration of the residue provided the target carbamate.

General Procedure 9 (GP 9): Urea Formation with Isopropenyl Carbamates

In analogy to *J. Org. Chem.* 2005, 70, 6960

The respective (hetero)aryl amine (1 eq.) was dissolved in THF (~4 mL per mmol amine) and treated with N-methylpyrrolidine (0.2 eq.) and the respective (hetero)aryl carbamic acid isopropenyl ester (1-1.5 eq.). The mixture was stirred overnight at 55° C. Extractive work-up followed by trituration and/or flash column chromatography and/or preparative HPLC purification provided the target urea.

General Procedure 10 (GP 10): Amide Formation

The respective (hetero)aryl amine (1 eq.) and the respective carboxylic acid (1.05 eq.) were dissolved in ethyl acetate (0.1-0.2 M) and treated with T3P (50% solution in ethyl acetate, 1.2 eq.). The resulting mixture was heated to 70° C. until final turnover (based on TLC or LCMS analysis). The reaction mixture was partitioned between ethyl acetate and water, the aqueous layers were reextracted with ethyl acetate, the combined organic layers were dried and concentrated in vacuo. The residue was optionally further purified by trituration or flash chromatography or preparative HPLC separation.

Synthesis of Key Intermediates

Intermediate 1.1

Preparation of N-[1-(3,5-Dibromo-pyridin-4-yl)-meth-(E)-ylidene]-N'-methyl-hydrazine

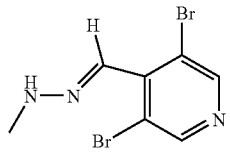

In analogy to GP 1, 2.15 g of 3,5-dibromo-pyridine-4-carbaldehyde (8.12 mmol, 1 eq; commercially available or prepared as described in U.S. Pat. No. 6,232,320 or WO2005110410) were dissolved in 36 mL 1-propyl alcohol, treated with 0.65 mL N-methyl hydrazine (12.17 mmol, 1.5 eq.) and heated to 100° C. for 30 min (employing a Biotage Initiator® microwave oven in batch mode). The reaction mixture was concentrated, the residue partitioned between water and ethyl acetate, the aqueous layer reextracted with ethyl acetate, the combined organic layers dried and concentrated in vacuo to yield 2.29 g of the desired product (7.82 mmol, 96% yield), which was used in the subsequent cyclization without further purification steps.

$^1$H-NMR (d$_6$-DMSO; 300 MHz): 8.57-8.63 (m, 3H); 7.22 (s, 1H); 2.86 (d, 3H).

MS (ESI): [M+H]$^+$=294 (Br$_2$ isotope pattern)

Intermediate 1.2

Preparation of 2-{N'-[1-(3,5-Dibromo-pyridin-4-yl)-meth-(E)-ylidene]-hydrazino}-ethanol

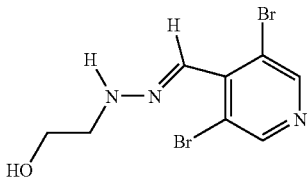 [SMILES: OCCN/N=C/c1c(Br)cncc1Br]

In analogy to GP1, 468 mg of 3,5-dibromo-pyridine-4-carbaldehyde (1.77 mmol, 1 eq; commercially available or prepared as described in U.S. Pat. No. 6,232,320 or WO2005110410) were dissolved in 8 mL 1-propyl alcohol, treated with 0.36 mL 2-hydrazino-ethanol (5.3 mmol, 3 eq.) and heated to 120° C. for 30 min (employing a Biotage Initiator® microwave oven). The reaction mixture was concentrated, the residue partitioned between water and ethyl acetate, the aqueous layer reextracted with ethyl acetate, the combined organic layers dried and concentrated in vacuo to yield 530 mg of the desired product (1.64 mmol, 93% yield), which was used in the subsequent cyclization without further purification steps.

$^1$H-NMR (d$_6$-DMSO; 300 MHz): 8.59 (s, 2H); 8.55 (t, 1H); 7.51 (s, 1H); 4.70 (t, 1H); 3.58 (q, 2H); 3.25 (q, 2H).

MS (ESI): [M+H]$^+$=324 (Br$_2$ isotope pattern)

Intermediate 1.3

Preparation of [1-(3,5-Dibromo-pyridin-4-yl)meth-(E)-ylidene]-hydrazine

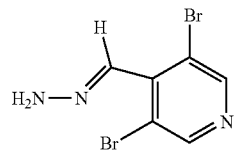 [SMILES: N/N=C/c1c(Br)cncc1Br]

In analogy to GP 1, 54 mg of 3,5-dibromo-pyridine-4-carbaldehyde (0.2 mmol, 1 eq; commercially available or prepared as described in U.S. Pat. No. 6,232,320 or WO2005110410) were dissolved in 1 mL 1-propyl alcohol, treated with 30 μL 80% hydrazine hydrate (0.61 mmol, 3 eq.) and heated to 120° C. for 30 min (employing a Biotage Initiator® microwave oven). The precipitate was filtered and washed with cold 1-propyl alcohol to yield 27 mg of the hydrazone (0.1 mmol, 50% yield).

$^1$H-NMR (d$_6$-DMSO; 400 MHz): 8.61 (s, 2H); 7.96 (s, 2H); 7.72 (s, 1H).

MS (LC-MS): >90% pure; [M+H]$^+$=279 (Br$_2$ isotope pattern)

Intermediate 1.4

Preparation of N'-[1-(3,5-Dibromo-pyridin-4-yl)-meth-(E)-ylidene]-hydrazinecarboxylic acid tert-butyl ester

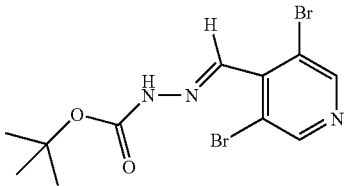 [SMILES: CC(C)(C)OC(=O)N/N=C/c1c(Br)cncc1Br]

In analogy to GP 1, 1.37 g of 3,5-dibromo-pyridine-4-carbaldehyde (5.17 mmol, 1 eq; commercially available or prepared as described in U.S. Pat. No. 6,232,320 or WO2005110410) were dissolved in 24 mL 1-propyl alcohol, treated with 2.05 g tert-butyl carbazate (15.5 mmol, 3 eq.) and heated to 120° C. for 30 min (employing a Biotage Initiator® microwave oven in batch mode). The precipitate was filtered and washed with cold 1-propyl alcohol to yield 1.66 g of the Boc-hydrazone (4.37 mmol, 85% yield).

¹H-NMR (d₆-DMSO; 400 MHz): 11.36 (br., 1H); 8.74 (s, 2H); 8.04 (s, 1H); 1.44 (s, 9H).

Intermediate 1.5

Preparation of N-[1-(3,5-Dibromo-pyridin-4-yl)-meth-(E)-ylidene]-N'-ethyl-hydrazine

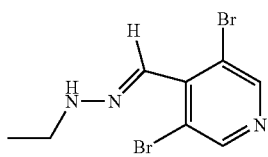

In analogy to GP 1, 2.65 g of 3,5-dibromo-pyridine-4-carbaldehyde (10 mmol, 1 eq; commercially available or prepared as described in U.S. Pat. No. 6,232,320 or WO2005110410) were dissolved in 32 mL 1-propyl alkohol, treated with 2.25 g N-ethyl hydrazine (oxalate salt; 15 mmol, 1.5 eq.) and heated to 100° C. for 30 min (employing a Biotage Initiator® microwave oven in batch mode). The reaction mixture was concentrated, the residue partitioned between conc. aq. sodium bicarbonate solution and ethyl acetate, the aqueous layer reextracted with ethyl acetate, the combined organic layers dried and concentrated in vacuo to yield 3.08 g of the desired product (10 mmol, quantitative yield), which was used in the subsequent cyclization without further purification steps.

¹H-NMR (d₆-DMSO; 300 MHz): 8.60 (s, 2H); 8.53 (t, 1H); 7.40 (s, 1H); 3.18 (dq, 2H); 1.16 (t, 3H).

Intermediate 2.1

Preparation of 4-Bromo-1-methyl-1H-pyrazolo[3,4-c]pyridine

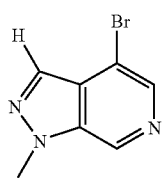

In analogy to GP 2, 5.34 g of N-[1-(3,5-Dibromo-pyridin-4-yl)-meth-(E)-ylidene]-N'-methyl-hydrazine (Intermediate 1.1, 18.23 mmol, 1 eq) were dissolved in 163 mL dry THF, treated at rt with 994 mg 50-60% sodium hydride (22.78 mmol, 1.2 eq) and subsequently refluxed for 90 min. The reaction mixture was quenched with water, extracted with ethyl acetate, the combined organic layers dried and concentrated in vacuo. The precipitate was filtered and subsequently triturated with diisopropylether to yield 1.71 g of the desired product. Flash column chromatography of the mother liquor provided a second batch of the analytically pure product.

¹H-NMR (d₆-DMSO; 400 MHz): 9.16 (s, 1H); 8.34 (s, 1H); 8.16 (s, 1H); 4.17 (s, 3H).

MS (ESI): [M+H]⁺=212 (Br isotope pattern).

Intermediate 2.2

Preparation of 2-(4-Bromo-pyrazolo[3,4-c]pyridin-1-yl)-ethanol

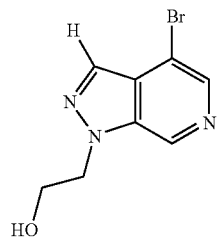 [SMILES: OCCn1ncc2c(Br)cncc21]

In analogy to GP2, 520 mg of 2-{N'-[1-(3,5-Dibromo-pyridin-4-yl)-meth-(E)-ylidene]-hydrazino}-ethanol (Intermediate 1.2, 1.61 mmol, 1 eq) were dissolved in 14 mL dry THF, treated at rt with 155 mg 50-60% sodium hydride (3.54 mmol, 2.2 eq) and subsequently refluxed for 90 min. The reaction mixture was quenched with water, extracted with ethyl acetate, the combined organic layers dried and concentrated in vacuo to yield 424 mg of a crude product, which was optionally further purified by trituration or flash column chromatography.

LC-MS: [M+H]⁺=243 (Br isotope pattern)

Intermediate 2.3

Preparation of 4-Bromo-1H-pyrazolo[3,4-c]pyridine

In analogy to GP 2, 578 mg of [1-(3,5-dibromo-pyridin-4-yl)-meth-(E)-ylidene]-hydrazine (Intermediate 1.3, 2.07 mmol, 1 eq) were dissolved in 18 mL dry THF, treated at rt with 200 mg 50-60% sodium hydride (4.56 mmol, 2.2 eq) and subsequently refluxed for 90 min. The reaction mixture was quenched with water, extracted with ethyl acetate, the combined organic layers dried and concentrated in vacuo.

MS (LC-MS): [M+H]⁺=198 (Br₂ isotope pattern)

Intermediate 2.4

Preparation of
4-Bromo-1-ethyl-1H-pyrazolo[3,4-c]pyridine

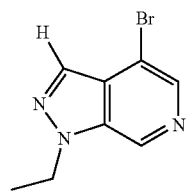

In analogy to GP 2, 2.1 g of Intermediate 1.5 (6.83 mmol, 1 eq) were dissolved in 60 mL dry THF, treated at rt with 372 mg 50-60% sodium hydride (8.53 mmol, 1.25 eq) and subsequently refluxed for 90 min. The reaction mixture was quenched with water, extracted with ethyl acetate, the combined organic layers dried and concentrated in vacuo. The precipitate was filtered and subsequently triturated with diisopropylether to yield 1.6 g of the desired product (quantitative yield).

$^1$H-NMR (d$_6$-DMSO; 400 MHz): 9.20 (s, 1H); 8.34 (s, 1H); 8.18 (s, 1H); 4.56 (q, 2H); 1.42 (t, 3H).

Intermediate 2.5

Preparation of 4-Bromo-1-(2-methoxy-ethyl)-1H-pyrazolo[3,4-c]pyridine

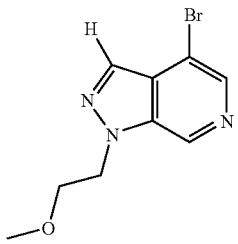

A solution of 675 mg of 2-(4-bromo-pyrazolo[3,4-c]pyridin-1-yl)-ethanol (Intermediate 2.2; 2.79 mmol, 1 eq.) in 33 mL THF was treated at rt with 183 mg sodium hydride (55-60% suspension; 4.18 mmol, 1.5 eq.) and stirred for 30 min upon which 0.194 mL methyl iodide (3.07 mmol, 1.1 eq.) were added and stirring was continued for 2 h. The reaction mixture was quenched with water, extracted with ethyl acetate, the combined organic layers were dried and concentrated in vacuo. Flash column chromatography provided 500 mg of the corresponding methyl ether target compound (1.95 mmol, 70% yield).

Intermediate 2.6

Preparation of 4-Bromo-1-(2-bromo-ethyl)-1H-pyrazolo[3,4-c]pyridine

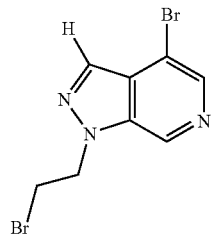 [SMILES: BrCCn1ncc2c(Br)cncc21]

A solution of 709 mg of 2-(4-bromo-pyrazolo[3,4-c]pyridin-1-yl)-ethanol (Intermediate 2.2; 2.93 mmol, 1 eq.) in 3 mL DMF was treated at rt with 1.93 g triphenylphosphine (7.32 mmol, 2.5 eq.) and 1.94 g carbon tetrabromide (5.86 mmol, 2 eq.) and stirred for 90 min at rt. The reaction mixture was quenched with water, extracted with DCM, the combined organic layers were dried and concentrated in vacuo. Flash column chromatography provided 290 mg of the bromo compound (0.95 mmol, 33% yield).

$^1$H-NMR (d$_6$-DMSO; 300 MHz): 9.25 (s, 1H); 8.37 (s, 1H); 8.27 (d, 1H); 4.98 (t, 2H); 3.96 (t, 2H).

Intermediate 2.7

Preparation of 4-Bromo-1-(2-methanesulfonyl-ethyl)-1H-pyrazolo[3,4-c]pyridine

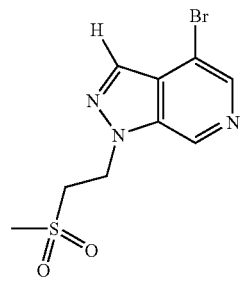 [SMILES: CS(=O)(=O)CCn1ncc2c(Br)cncc21]

100 mg of 4-Bromo-1-(2-bromo-ethyl)-1H-pyrazolo[3,4-c]pyridine (Intermediate 2.6; 0.33 mmol, 1 eq.) were dissolved in 5 mL ethanol and treated with 150 mg sodium methyl sulfinate (1.5 mmol, 4.5 eq.) and heated to 120° C. for 4 h in a Biotage Initiator microwave oven. The reaction mixture was quenched with water, extracted with DCM, the combined organic layers were dried and concentrated in vacuo to provide the crude Intermediate 2.7, which was used without further purification in the subsequent transformations.

MS (LC-MS): [M+H]$^+$=304/306 (Br isotope pattern)

Intermediate 3.1

Preparation of 3-(1-Methyl-1H-pyrazolo[3,4-c]pyridin-4-ylethynyl)-phenylamine

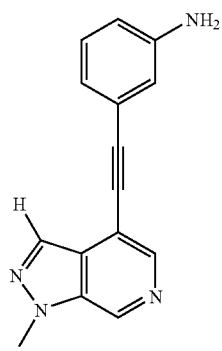 [SMILES: Cn1ncc2c(C#Cc3cccc(N)c3)cncc21]

In an adaption of GP 3c, 639 mg of 4-bromo-1-methyl-1H-pyrazolo[3,4-c]pyridine (Intermediate 2.1, 3 mmol, 1 eq), 931 mg 3-trimethylsilanylethynyl-phenylamine (4.9 mmol, 1.6 eq.), 106 mg dichlorobis(triphenylphosphine)palladium (II) ($PdCl_2(PPh_3)_2$) (0.15 mmol, 5 mol %) and 115 mg copper (I) iodide (0.6 mmol, 0.2 eq.) were dissolved in 15 mL THF (0.2 M) and treated with 3.6 mL tetra-n-butylammonium fluoride solution (1.0 M in THF, 3.6 mmol, 1.2 eq.). The resulting mixture was heated to 80° C. in a Biotage Initiator microwave oven for 30 min. Extractive work-up followed by column chromatography provided the target compound.

$^1$H-NMR ($d_6$-DMSO; 300 MHz): 9.23 (br. s, 1H); 8.44 (br. s, 1H); 8.30 (s, 1H); 7.11 (t, 1H); 6.81-6.86 (m, 2H); 6.66 (ddd, 1H); 5.31 (br. s, 2H); 4.22 (s, 3H).

Intermediate 3.2

Preparation of 4-Methyl-3-(1-methyl-1H-pyrazolo[3,4-c]pyridin-4-ylethynyl)-phenylamine

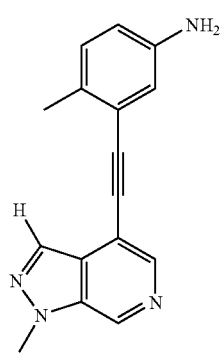 [SMILES: Cc1ccc(N)cc1C#Cc1cncc2c1cnn2C]

In an adaption of GP 3c, 640 mg of 4-bromo-1-methyl-1H-pyrazolo[3,4-c]pyridine (Intermediate 2.1, 3 mmol, 1 eq), 1000 mg 3-trimethylsilanylethynyl-phenylamine (4.92 mmol, 1.63 eq.), 106 mg dichlorobis(triphenylphosphine)palladium (II) ($PdCl_2(PPh_3)_2$) (0.15 mmol, 5 mol %) and 115 mg copper (I) iodide (0.6 mmol, 0.2 eq.) were dissolved in 15 mL THF (0.2 M) and treated with 3.6 mL tetra-n-butylammonium fluoride solution (1.0 M in THF, 3.6 mmol, 1.2 eq.). The resulting mixture was heated to 80° C. in a Biotage Initiator microwave oven for 30 min. Extractive work-up followed by column chromatography provided the 460 mg of the target compound (58% yield).

$^1$H-NMR ($d_6$-DMSO; 300 MHz): 9.15 (br. s, 1H); 8.37 (br. s, 1H); 8.20 (s, 1H); 6.96 (d, 1H); 6.79 (d, 1H); 6.55 (dd, 1H); 5.02 (br. s, 2H); 4.18 (s, 3H); 2.32 (s, 3H).

Intermediate 3.3

Preparation of 4-Fluoro-3-(1-methyl-1H-pyrazolo[3,4-c]pyridin-4-ylethynyl)-phenylamine

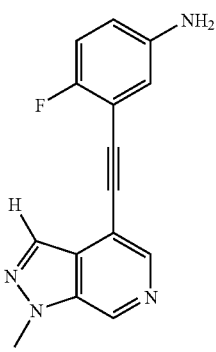 [SMILES: Cn1ncc2c(C#Cc3cc(N)ccc3F)cncc21]

In an adaption of GP 3c, 1000 mg of 4-bromo-1-methyl-1H-pyrazolo[3,4-c]pyridine (Intermediate 2.1, 4.7 mmol, 1 eq), 1590 mg 4-fluoro-3-trimethylsilanylethynyl-phenylamine (7.69 mmol, 1.63 eq.), 165 mg dichlorobis(triphenylphosphine)palladium (II) ($PdCl_2(PPh_3)_2$) (0.24 mmol, 5 mol %) and 179 mg copper (I) iodide (0.94 mmol, 0.2 eq.) were dissolved in 8 mL THF (0.2 M) and treated with 16.5 mL tetra-n-butylammonium fluoride solution (1.0 M in THF, 16.5 mmol, 3.5 eq.). The resulting mixture was heated to 80° C. in a Biotage Initiator microwave oven for 30 min. Extractive work-up delivered the crude product which was used without further purification.

¹H-NMR (d₆-DMSO; 300 MHz): 9.20 (br. s, 1H); 8.40 (br. s, 1H); 8.19 (s, 1H); 6.98 (t, 1H); 6.79 (dd, 1H); 6.63 (ddd, 1H); 5.15 (br. s, 2H); 4.18 (s, 3H).

SYNTHESIS OF EXAMPLE COMPOUNDS

Example Compound 1.1

Preparation of N-[3-(1-Methyl-1H-pyrazolo[3,4-c]pyridin-4-ylethynyl)-phenyl]-benzamide

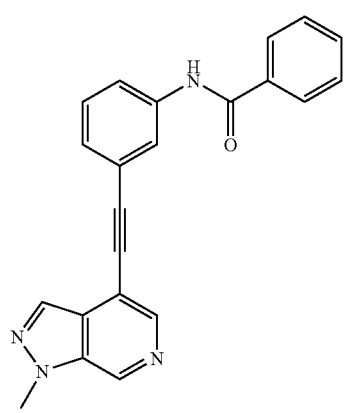 [SMILES: Cn1ncc2c(C#Cc3cccc(NC(=O)c4ccccc4)c3)cncc21]

In an adaption of GP 3c, 60 mg of 4-bromo-1-methyl-1H-pyrazolo[3,4-c]pyridine (Intermediate 2.1, 0.28 mmol, 1 eq), 140 mg N-(3-trimethylsilanylethynyl-phenyl)-benzamide (0.48 mmol, 1.68 eq.), 10 mg dichlorobis(triphenylphosphine)palladium (II) (PdCl$_2$(PPh$_3$)$_2$) (0.014 mmol, 5 mol %) and 10.8 mg copper (I) iodide (0.057 mmol, 0.2 eq.) were dissolved in 1.4 mL THF (0.2 M) and treated with 0.35 mL tetra-n-butylammonium fluoride solution (1.0 M in THF, 0.35 mmol, 1.25 eq.). The resulting mixture was heated to 80° C. in a Biotage Initiator microwave oven for 30 min. Extractive work-up followed by column chromatography and preparative HPLC purification provided the target compound.

¹H-NMR (d₆-DMSO; 300 MHz): 10.41 (s, 1H); 9.25 (br. s, 1H); 8.49 (br. s, 1H); 8.37 (s, 1H); 8.17 (s, 1H); 8.00 (d, 2H); 7.87 (dt, 1H); 7.53-7.66 (m, 3H); 7.44-7.51 (m, 2H); 4.24 (s, 3H).

Example Compound 1.2

Preparation of N-[4-Methyl-3-(1-methyl-1H-pyrazolo[3,4-c]pyridin-4-ylethynyl)-phenyl]-benzamide

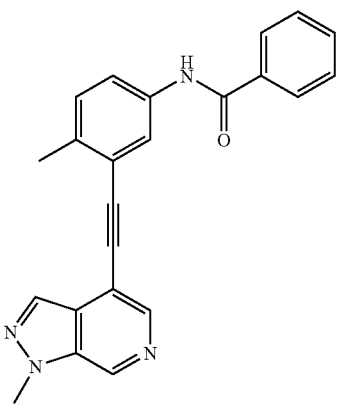 [SMILES: Cc1ccc(NC(=O)c2ccccc2)cc1C#Cc1cncc2c1cnn2C]

In analogy to GP 10, 78 mg of 4-methyl-3-(1-methyl-1H-pyrazolo[3,4-c]pyridin-4-ylethynyl)-phenylamine (Intermediate 3.2; 0.3 mmol, 1 eq.) were treated with 38 mg benzoic acid (0.31 mmol, 1.05 eq.) and 0.21 mL T3P solution (50% in ethyl acetate, 0.36 mmol, 1.2 eq.) in 2.2 mL ethyl acetate to yield the target product.

¹H-NMR (d₆-DMSO; 300 MHz): 10.33 (s, 1H); 9.23 (s, 1H); 8.49 (s, 1H); 8.30 (s, 1H); 8.12 (d, 1H); 7.97-8.02 (m, 2H); 7.76 (dd, 1H); 7.53-7.65 (m, 3H); 7.37 (d, 1H); 4.24 (s, 3H); 2.54 (s, 3H).

The following example compounds 1.3 to 1.9 were prepared in analogy to Example compound 1.2 and GP 10 by amide formation of the respective intermediates 3.1 or 3.2 or 3.3 with readily available carboxylic acids.

| Example | Structure | Name | Analytical data |
|---|---|---|---|
| 1.3 | 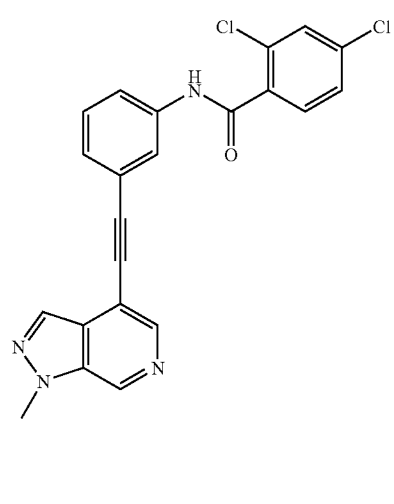 [SMILES: Cn1ncc2c(C#Cc3cccc(NC(=O)c4ccc(Cl)cc4Cl)c3)cncc21] | 2,4-Dichloro-N-[3-(1-methyl-1H-pyrazolo[3,4-c]pyridin-4-ylethynyl)-phenyl]-benzamide | ¹H-NMR: (d6-DMSO, 300 MHz) 10.74 (s, 1 H); 9.23 (s, 1 H); 8.48 (s, 1 H); 8.37 (s, 1 H); 8.09 (s, 1 H); 7.81 (d, 1 H); 7.71-7.74 (m, 1 H); 7.69 (d, 1 H); 7.59 (dd, 1 H); 7.45-7.51 (m, 2 H); 4.24 (s, 3 H).<br>MS (ESI): [M + H]⁺ = 421/423 (Cl₂ isotope pattern). |

| Example | Structure | Name | Analytical data |
|---|---|---|---|
| 1.4 | 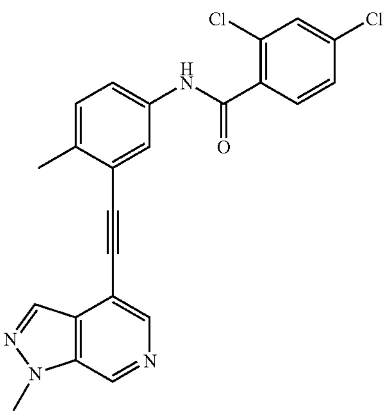 [SMILES: Cc1ccc(NC(=O)c2ccc(Cl)cc2Cl)cc1C#Cc1cncc2c1cnn2C] | 2,4-Dichloro-N-[4-methyl-3-(1-methyl-1H-pyrazolo[3,4-c]pyridin-4-ylethynyl)-phenyl]-benzamide | $^1$H-NMR: (d6-DMSO, 300 MHz) 10.59 (s, 1 H); 9.19 (s, 1 H); 8.44 (s, 1 H); 8.25 (s, 1 H); 8.00 (d, 1 H); 7.75 (d, 1 H); 7.63 (d, 1 H); 7.55 (td, 2 H); 7.33 (d, 1 H); 4.19 (s, 3 H). MS (ESI): [M + H]$^+$ = 435/437 (Cl$_2$ isotope pattern). |
| 1.5 | 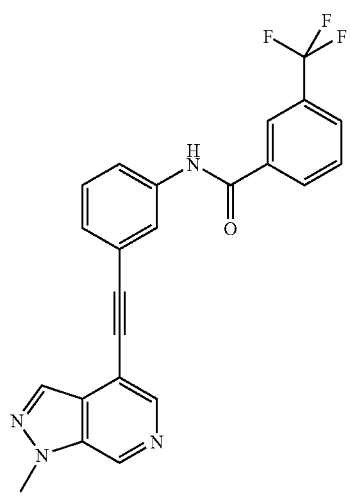 [SMILES: Cn1ncc2c(C#Cc3cccc(NC(=O)c4cccc(C(F)(F)F)c4)c3)cncc21] | N-[3-(1-Methyl-1H-pyrazolo[3,4-c]pyridin-4-ylethynyl)-phenyl]-3-trifluoromethyl-benzamide | $^1$H-NMR: (d6-DMSO, 300 MHz) 10.62 (s, 1 H); 9.23 (s, 1 H); 8.48 (s, 1 H); 8.37 (s, 1 H); 8.34 (s, 1 H); 8.30 (d, 1 H); 8.14 (s, 1 H); 8.00 (d, 1 H); 7.80-7.90 (m, 2 H); 7.47-7.54 (m, 2 H); 4.24 (s, 3 H). MS (ESI): [M + H]$^+$ = 421. |
| 1.6 | 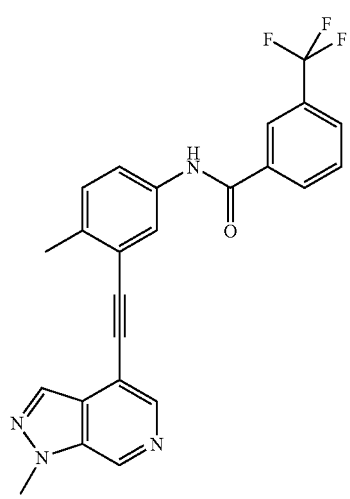 [SMILES: Cc1ccc(NC(=O)c2cccc(C(F)(F)F)c2)cc1C#Cc1cncc2c1cnn2C] | N-[4-Methyl-3-(1-methyl-1H-pyrazolo[3,4-c]pyridin-4-ylethynyl)-phenyl]-3-trifluoromethyl-benzamide | $^1$H-NMR: (d6-DMSO, 300 MHz) 10.50 (s, 1 H); 9.18 (s, 1 H); 8.43 (s, 1 H); 8.29 (s, 1 H); 8.26 (s, 1 H); 8.24 (s, 1 H); 8.04 (d, 1 H); 7.95 (d, 1 H); 7.78 (t, 1 H); 7.72 (dd, 1 H); 7.34 (d, 1 H); 4.19 (s, 3 H). MS (ESI): [M + H]$^+$ = 435. |

-continued

| Example | Structure | Name | Analytical data |
|---|---|---|---|
| 1.7 | 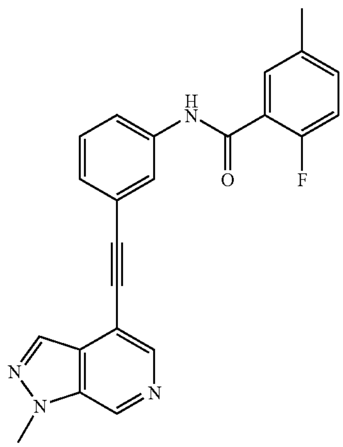 [SMILES: Cc1ccc(F)c(C(=O)Nc2cccc(C#Cc3cncc4c3cnn4C)c2)c1] | 2-Fluoro-5-methyl-N-[3-(1-methyl-1H-pyrazolo[3,4-c]pyridin-4-ylethynyl)-phenyl]-benzamide | $^1$H-NMR: (d6-DMSO, 300 MHz) 10.55 (s, 1 H); 9.23 (s, 1 H); 8.48 (s, 1 H); 8.37 (s, 1 H); 8.11 (s, 1 H); 7.74-7.80 (m, 1 H); 7.46-7.52 (m, 3 H); 7.40 (ddd, 1 H); 7.26 (dd, 1 H); 4.24 (s, 3 H); 2.36 (s, 3 H). MS (ESI): [M + H]$^+$ = 385. |
| 1.8 | 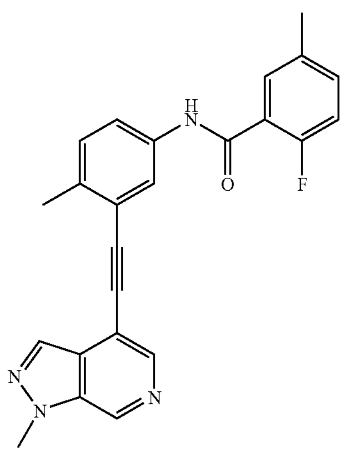 [SMILES: Cc1ccc(F)c(C(=O)Nc2ccc(C)c(C#Cc3cncc4c3cnn4C)c2)c1] | 2-Fluoro-5-methyl-N-[4-methyl-3-(1-methyl-1H-pyrazolo[3,4-c]pyridin-4-ylethynyl)-phenyl]-benzamide | $^1$H-NMR: (d6-DMSO, 300 MHz) 10.40 (s, 1 H); 9.19 (s, 1 H); 8.44 (s, 1 H); 8.25 (s, 1 H); 8.01 (d, 1 H); 7.61 (dd, 1 H); 7.44 (dd, 1 H); 7.30-7.37 (m, 2 H); 7.20 (dd, 1 H); 4.19 (s, 3 H); 2.31 (s, 3 H). MS (ESI): [M + H]$^+$ = 399. |
| 1.9 | 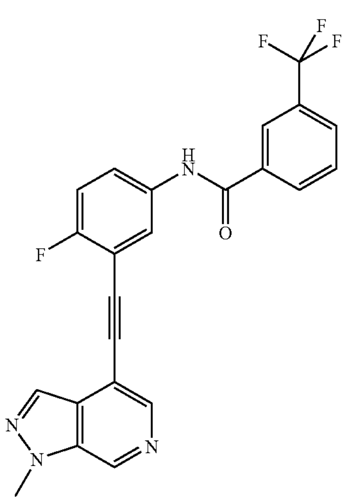 [SMILES: Cn1ncc2c(C#Cc3cc(NC(=O)c4cccc(C(F)(F)F)c4)ccc3F)cncc21] | N-[4-Fluoro-3-(1-methyl-1H-pyrazolo[3,4-c]pyridin-4-ylethynyl)-phenyl]-3-trifluoromethyl-benzamide | $^1$H-NMR: (d6-DMSO, 400 MHz) 10.62 (s, 1 H); 9.25 (s, 1 H); 8.47 (s, 1 H); 8.29 (s, 1 H); 8.26 (s, 1 H); 8.25 (d, 1 H); 8.14 (dd, 1 H); 7.96 (d, 1 H); 7.84 (ddd, 1 H); 7.78 (t, 1 H); 7.40 (t, 1 H); 4.21 (s, 3 H). MS (ESI): [M + H]$^+$ = 439. |

Example Compound 2.1

Preparation of 1-[3-(1-Methyl-1H-pyrazolo[3,4-c]pyridin-4-ylethynyl)-phenyl]-3-phenyl-urea

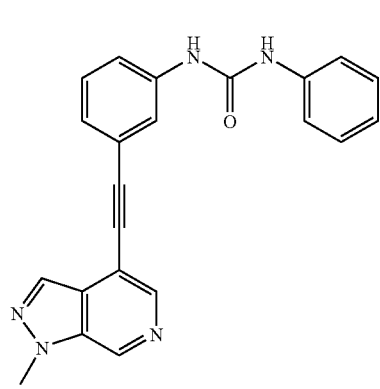 [SMILES: Cn1ncc2c(C#Cc3cccc(NC(=O)Nc4ccccc4)c3)cncc21]

In analogy to GP 5, 100 mg of 3-(1-methyl-1H-pyrazolo[3,4-c]pyridin-4-ylethynyl)-phenylamine (Intermediate 3.1, 0.26 mmol, 1 eq.) were treated with 31 μL phenyl isocyanate (0.29 mmol, 1.1 eq.) in 2.6 mL DCM at rt. Aqueous work-up followed by HPLC purification provided the target compound.

$^1$H-NMR (d$_6$-DMSO; 300 MHz): 9.18 (br. s, 1H); 8.82 (s, 1H); 8.74 (s, 1H); 8.49 (br. s, 1H); 8.33 (s, 1H); 7.84 (s, 1H); 7.40-7.45 (m, 3H); 7.35 (t, 1H); 7.24-7.29 (m, 3H); 6.95 (t, 1H); 4.19 (s, 3H).

MS (ESI): [M+H]$^+$=368.

Example Compound 2.2

Preparation of 1-[4-Methyl-3-(1-methyl-1H-pyrazolo[3,4-c]pyridin-4-ylethynyl)-phenyl]-3-phenyl-urea

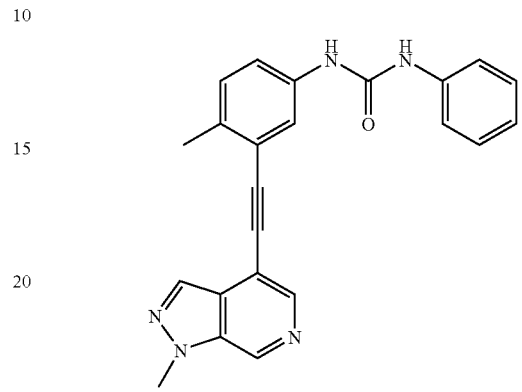

In analogy to GP 5, 200 mg of 4-methyl-3-(1-methyl-1H-pyrazolo[3,4-c]pyridin-4-ylethynyl)-phenylamine (Intermediate 3.2, 0.4 mmol, 1 eq.) were treated with 47 μL phenyl isocyanate (0.44 mmol, 1.1 eq.) in 4 mL DCM at rt. Aqueous work-up followed by HPLC purification provided the target compound.

$^1$H-NMR (d$_6$-DMSO; 300 MHz): 9.23 (br. s, 1H); 8.74 (s, 1H); 8.72 (s, 1H); 8.48 (br. s, 1H); 8.31 (s, 1H); 7.84 (d, 1H); 7.48 (d, 1H); 7.36 (dd, 1H); 7.27-7.32 (m, 3H); 6.98 (tt, 1H); 4.24 (s, 3H); 2.52 (s, 3H; partially obscured by DMSO signal).

MS (ESI): [M+H]$^+$=382.

The following example compounds 2.3 to 2.6 were prepared in analogy to example compound 2.1 and 2.2 and GP 5 by urea formation of the respective intermediates 3.1 or 3.2 or 3.3 with commercially available isocyanates.

| Example | Structure | Name | Analytical data |
|---|---|---|---|
| 2.3 | 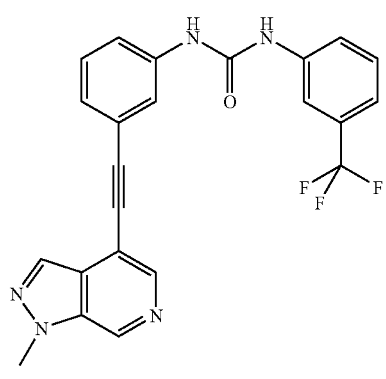 [SMILES: Cn1ncc2c(C#Cc3cccc(NC(=O)Nc4cccc(C(F)(F)F)c4)c3)cncc21] | 1-[3-(1-Methyl-1H-pyrazolo[3,4-c]pyridin-4-ylethynyl)-phenyl]-3-(3-trifluoromethyl-phenyl)-urea | $^1$H-NMR: (d6-DMSO, 400 MHz) 9.18 (br. s, 1 H); 9.16 (s, 1 H); 8.98 (s, 1 H); 8.43 (br. s, 1 H); 8.34 (s, 1 H); 8.01 (s, 1 H); 7.85 (s, 1 H); 7.56 (d, 1 H); 7.49 (t, 1 H); 7.43 (d, 1 H); 7.36 (t, 1 H); 7.28-7.32 (m, 2 H); 4.19 (s, 3 H). MS (ESI): [M + H]$^+$ = 436. |

| Example | Structure | Name | Analytical data |
|---|---|---|---|
| 2.4 | 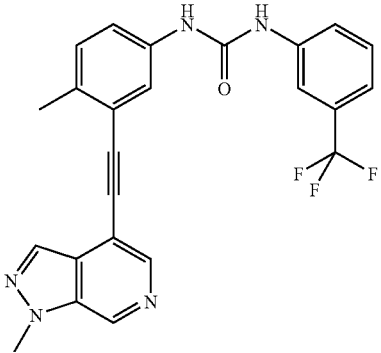 [SMILES: Cc1ccc(NC(=O)Nc2cccc(C(F)(F)F)c2)cc1C#Cc1cncc2c1cnn2C] | 1-[4-Methyl-3-(1-methyl-1H-pyrazolo[3,4-c]pyridin-4-ylethynyl)-phenyl]-3-(3-trifluoromethyl-phenyl)-urea | $^1$H-NMR: (d6-DMSO, 300 MHz) 9.23 (br. s, 1 H); 9.14 (s, 1 H); 8.80 (s, 1 H); 8.49 (br. s, 1 H); 8.31 (s, 1 H); 8.05 (s, 1 H); 7.85 (s, 1 H); 7.60 (d, 1 H); 7.53 (t, 1 H); 7.38 (dd, 1 H); 7.31 (t, 2 H); 4.24 (s, 3 H); 3H obscured by DMSO signal. MS (ESI): [M + H]$^+$ = 450. |
| 2.5 | 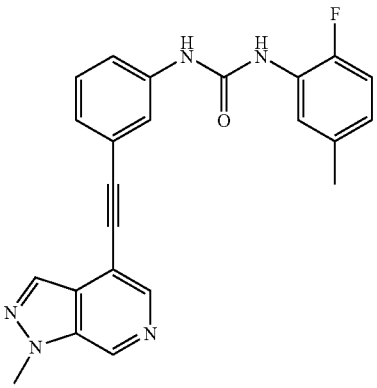 [SMILES: Cc1ccc(F)c(NC(=O)Nc2cccc(C#Cc3cncc4c3cnn4C)c2)c1] | 1-(2-Fluoro-5-methyl-phenyl)-3-[3-(1-methyl-1H-pyrazolo[3,4-c]pyridin-4-ylethynyl)-phenyl]-urea | 1H-NMR: (d6-DMSO, 300 MHz) 9.20 (s, 1 H); 9.18 (s, 1 H); 8.53 (d, 1 H); 8.43 (s, 1 H); 8.33 (s, 1 H); 7.95 (dd, 1 H); 7.87 (s, 1 H); 7.28-7.38 (m, 3 H); 6.75-6.80 (m, 1 H); 7.08 (dd, 1 H); 4.19 (s, 3 H); 2.23 (s, 3 H). MS (ESI): [M + H]$^+$ = 400. |
| 2.6 | 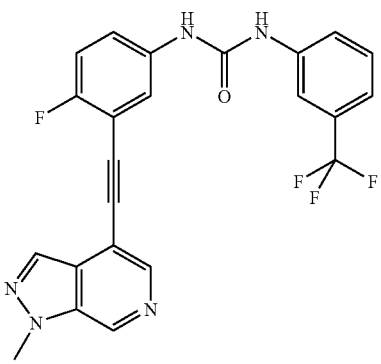 [SMILES: Cn1ncc2c(C#Cc3cc(NC(=O)Nc4cccc(C(F)(F)F)c4)ccc3F)cncc21] | 1-[4-Fluoro-3-(1-methyl-1H-pyrazolo[3,4-c]pyridin-4-ylethynyl)-phenyl]-3-(3-trifluoromethyl-phenyl)-urea | $^1$H-NMR: (d6-DMSO, 300 MHz) 9.23 (s, 1 H); 9.15 (s, 1 H); 8.97 (s, 1 H); 8.46 (s, 1 H); 8.26 (s, 1 H); 7.99 (br. s, 1 H); 7.88 (dd, 1 H); 7.56 (d, 1 H); 7.44-7.50 (m, 2 H); 7.28-7.32 (m, 2 H); 4.20 (s, 3 H). MS (ESI): [M + H]$^+$ = 454. |

Example Compound 3.1

Preparation of 1-[2-(3-Fluoro-phenyl)-5-isopropyl-2H-pyrazol-3-yl]-3-[3-(1-methyl-1H-pyrazolo[3,4-c]pyridin-4-ylethynyl)-phenyl]-urea

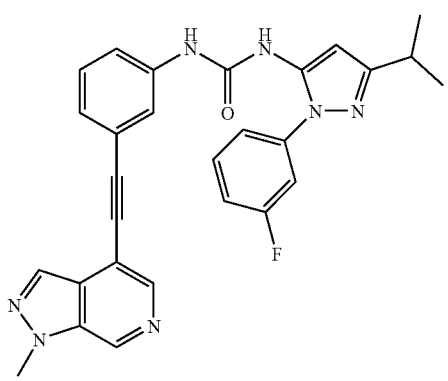 [SMILES: CC(C)c1cc(NC(=O)Nc2cccc(C#Cc3cncc4c3cnn4C)c2)n(-c2cccc(F)c2)n1]

In analogy to GP 7, 150 mg of 3-(1-methyl-1H-pyrazolo[3,4-c]pyridin-4-ylethynyl)-phenyl-amine (Intermediate 3.1, 0.6 mmol, 1 eq.) were dissolved in 2 mL pyridine and 7 mL THF, treated with 205 mg of [2-(3-fluoro-phenyl)-5-isopropyl-2H-pyrazol-3-yl]-carbamic acid phenyl ester (0.6 mmol, 1 eq.). The reaction mixture was heated to 100° C. for 15 min (Biotage Initiator). The reaction mixture was concentrated and the target compound was isolated by preparative HPLC purification.

$^1$H-NMR (d$_6$-DMSO; 400 MHz): 9.19 (br. s, 2H); 8.57 (br. s, 1H); 8.41 (br. s, 1H); 8.31 (s, 1H); 7.81 (s, 1H); 7.51-7.56 (m, 1H); 7.27-7.42 (m, 5H); 7.20-7.24 (m, 1H); 6.33 (s, 1H); 4.19 (s, 3H); 2.87 (sept., 1H); 1.20 (d, 6H).

MS (LC-MS-ESI): [M+H]$^+$=494.

The following example compound 3.2 was synthesized in analogy to GP 7 and example compound 3.1 by reaction of Intermediate 3.1 with the respective phenyl carbamate.

Example Compound 4.1

Preparation of 1-[4-(4-Methyl-piperazin-1-ylmethyl)-3-trifluoromethyl-phenyl]-3-[3-(1-methyl-1H-pyrazolo[3,4-c]pyridin-4-ylethynyl)-phenyl]-urea

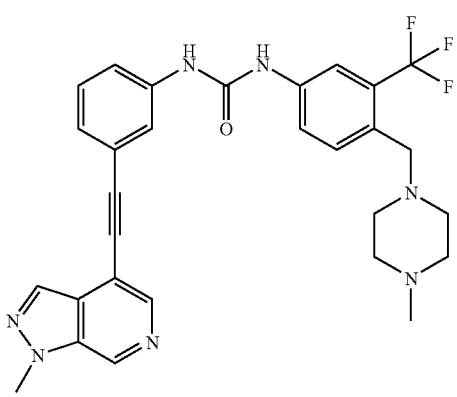 [SMILES: CN1CCN(Cc2ccc(NC(=O)Nc3cccc(C#Cc4cncc5c4cnn5C)c3)cc2C(F)(F)F)CC1]

124 mg of 3-(1-methyl-1H-pyrazolo[3,4-c]pyridin-4-ylethynyl)-phenylamine (Intermediate 3.1, 0.5 mmol, 1 eq.) were dissolved in 9 mL acetonitrile and treated with 163 mg of 4-(4-methyl-piperazin-1-ylmethyl)-3-trifluoromethyl-phenylamine (0.6 mmol, 1 eq.) and 59 mg of triphosgene (0.2 mmol). The reaction mixture was stirred at rt for 4 h after which the same amounts of triphosgene and 4-(4-methyl-piperazin-1-ylmethyl)-3-trifluoromethyl-phenylamine were added once more and stirring at rt was continued for 16 h. Extractive work-up followed by HPLC purification provided the pure target compound.

$^1$H-NMR (d$_6$-DMSO; 300 MHz): 9.18 (s, 1H); 9.07 (br. s, 1H); 8.92 (br. s, 1H); 8.43 (s, 1H); 8.33 (s, 1H); 7.95 (br. s,

| Example | Structure | Name | Analytical data |
|---|---|---|---|
| 3.2 | 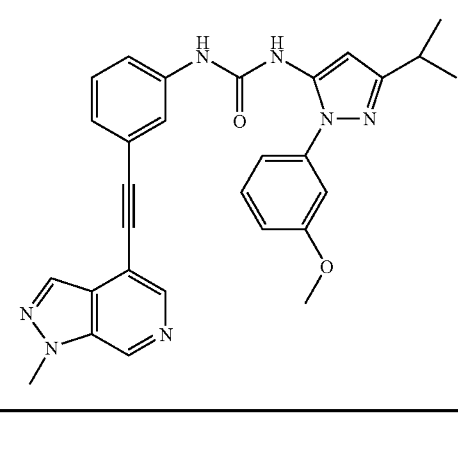 | 1-[5-Isopropyl-2-(3-methoxy-phenyl)-2H-pyrazol-3-yl]-3-[3-(1-methyl-1H-pyrazolo[3,4-c]pyridin-4-ylethynyl)-phenyl]-urea | $^1$H-NMR: (d6-DMSO, 400 MHz) 9.21 (s, 1 H); 9.18 (br. s, 1 H); 8.48 (s, 1 H); 8.42 (br. s, 1 H); 8.31 (s, 1 H); 7.81 (s, 1 H); 7.27-7.42 (m, 4 H); 7.06-7.08 (m, 2 H); 6.95 (dd, 1 H); 6.32 (s, 1 H); 4.19 (s, 3 H); 3.77 (s, 3 H); 2.86 (sept., 1 H); 1.20 (d, 6 H). MS (ESI): [M + H]$^+$ = 506. |

1H); 7.84 (br. s, 1H); 7.60 (d, 1H); 7.54 (dd, 1H); 7.43 (dt, 1H); 7.36 (t, 1H); 7.30 (dt, 1H); 4.19 (s, 3H); 3.49 (s, 2H); 2.22-2.39 (m, 8H); 2.12 (s, 3H).

Description of Biological Assays

A selection of assays to profile compounds of the present invention is described in the following paragraphs.

Assay 1: Tie2 ELISA Assay

Cellular activity of compounds of the present invention as inhibitors of Tie2 kinase activity was measured employing a Tie2 ELISA assay as described in the following paragraphs. Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP for detection.

Materials:
  96 well tissue culture plate, sterile, Greiner
  96 well FluoroNunc plate MaxiSorp Surface C, Nunc
  96 well plate polypropylene for compound dilution in DMSO
  CHO Tie2/DHFR (transfected cells)
  PBS–; PBS++, DMSO
  MEM alpha Medium with Glutamax-I without Ribonucleosides and Deoxyribonucleosides (Gibco #32561-029) with 10% FCS after dialysis! and 1% PenStrep
  Lysis buffer: 1 Tablet "Complete" protease inhibitor
    1 cap Vanadate (1 mL>40 mg/mL; working solution 2 mM)
    ad 50 mL with Duschl-Puffer
    pH 7.6
  Anti-Tie2-antibody 1: 425 in Coating Buffer pH 9.6
    Stock solution: 1.275 mg/mL>working: 3 µg/mL
  PBST: 2 bottles PBS(10×)+10 ml Tween, fill up with VE-water
  RotiBlock 1:10 in VE-water
  Anti-Phosphotyrosine HRP-Conjugated 1:10000 in 3% TopBlock
    3% TopBlock in PBST
  BM Chemiluminescence ELISA Substrate (POD) solution B 1:100 solution A
  SF9 cell culture medium
  Ang2-Fc in SF9 cell culture medium Cell Experiment:
  Dispense $5 \times 10^4$ cells/well/98 µL in 96 well tissue culture plate
  Incubate at 37° C./5% $CO_2$
  After 24 h add compounds according to desired concentrations
  Add also to control and stimulated values without compounds 2 µL DMSO
  And mix for a few min at room temperature
  Add 100 µL Ang2-Fc to all wells except control, which receives insect medium
  Incubate 20 min at 37° C.
  Wash 3× with PBS++
  Add 100 µl Lysis buffer/well and shake a couple of min at room temperature
  Store lysates at 20° C. before utilizing for the ELISA Performance of Sandwich-ELISA
  Coat 96 well FluoroNunc Plate MaxiSorp Surface C with anti-Tie2 mAb 1:425 in Coating buffer pH 9.6; 100 µL/well overnight at 4° C.
  Wash 2× with PBST
  Block plates with 250 µL/well RotiBlock 1:10 in VE-water
  Incubate for 2 h at room temperature or overnight at 4° C. shaking
  Wash 2× in PBST
  Add thawed lysates to wells and incubate overnight shaking at 4° C.
  Wash 2× with PBST
  Add 100 µL/well anti-Phosphotyrosine HRP-Conjugated 1:10000 in 3% TopBlock
  (3% TopBlock in PBST) and incubate overnight under shaking
  Wash 6× with PBST
  Add 100 µL/well BM Chemiluminescence ELISA Substrate (POD) solutions 1 and 2 (1:100)
  Determine luminescence with the LumiCount.

Assay 2: Tie-2-Kinase HTRF-Assay

Tie2-inhibitory activity of compounds of the present invention was quantified employing two Tie2 HTRF assay as described in the following paragraphs.

A recombinant fusion protein of GST and the intracellular domains of Tie-2, expressed in insect cells (Hi-5) and purified by Glutathion-Sepharose affinity chromatography was used as kinase. Alternatively, commercially available GST-Tie2-fusion protein (Upstate Biotechnology, Dundee, Scotland) can be used As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany). Detection of phosphorylated product is achieved specifically by a trimeric detection complex consisting of the phosphorylated substrate, streptavidin-XLent (SA-XLent) which binds to biotin, and Europium Cryptate-labeled anti-phosphotyrosine antibody PT66 which binds to phosphorylated tyrosine.

Tie-2 (3.5 ng/measurement point) was incubated for 60 min at 22° C. in the presence of 10 µM adenosine-tri-phosphate (ATP) and 1 µM substrate peptide (biotin-Ahx-EPKD-DAYPLYSDFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointemational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0 (% inhibition, all other assay components but no enzyme=100% inhibition) and $IC_{50}$ values were calculated by a 4 parameter fit using an inhouse software.

Assay 3: Alternative Tie-2-Kinase HTRF-Assay

A recombinant fusion protein of GST and the intracellular domains of Tie-2, expressed in insect cells (Hi-5) and purified by Glutathion-Sepharose affinity chromatography was used as kinase. As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany).

For activation, Tie-2 was incubated at a conc. 12.5 ng/µl of for 20 min at 22° C. in the presence of 250 µM adenosine-tri-phosphate (ATP) in assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml)].

For the subsequent kinase reaction, the preactivated Tie-2 (0.5 ng/measurement point) was incubated for 20 min at 22° C. in the presence of 10 µM adenosine-tri-phosphate (ATP) and 1 µM substrate peptide (biotin-Ahx-EPKDDAYPLYS-DFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 4: Insulin Receptor HTRF Assay

Inhibitory activity of compounds against the kinase activity of the insulin receptor was quantified employing the Ins-R HTRF assay as described in the following paragraphs.

GST-tagged recombinant kinase domain of the human insuline receptor (Ins-R, purchase from ProQinase, Freiburg, Germany) expressed in SF-9 cells was used as kinase. As substrate for the kinase reaction biotinylated poly-(Glu, Tyr) (Cis biointernational, France) was used.

Ins-R was incubated for 20 min at 22° C. in the presence of different concentrations of test compounds in 5 µl assay buffer [50 mM Hepes/NaOH pH 7, 15 mM $MnCl_2$, 1 mM dithiothreitol, 0.1 µM sodium ortho-vanadate, 0.015% (v/v) PEG20000, 10 µM adenosine-tri-phosphate (ATP), 0.3 µg/ml substrate, 1% (v/v) dimethylsulfoxide]. The concentration of Ins-R was adjusted depending of the activity of the enzyme lot and was chosen appropriate to have the assay in the linear range, typical concentrations were in the range of 10 pg/µl. The reaction was stopped by the addition of 5 µl of a solution of HTRF detection reagents (0.1 µM streptavidine-XLent and 1 nM PT66-Eu-Chelate, an europium-chelate labelled anti-phospho-tyrosine antibody from Perkin Elmer) in an aqueous EDTA-solution (80 mM EDTA, 0.2% (w/v) bovine serum albumin in 50 mM HEPES/NaOH pH 7.0).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Assay 5: VEGFR2 HTRF Assay

VEGFR2 inhibitory activity of compounds of the present invention was quantified employing the VEGFR2 HTRF assay as described in the following paragraphs.

GST-tagged recombinant kinase domain of the human VEGFR2 expressed in SF-9 cells was used as kinase. As substrate for the kinase reaction the biotinylated peptide biotin-Ahx-DFGLARDMYDKEYYSVG (C-terminus in acid form) was used which can be purchased e.g. form the company Biosynthan GmbH (Berlin-Buch, Germany). VEGFR2 was incubated for 45 min at 22° C. in the presence of different concentrations of test compounds in 5 µl assay buffer [50 mM Hepes/NaOH pH 7.0, 25 mM $MgCl_2$, 5 mM $MnCl_2$, 1.0 mM dithiothreitol, 0.1 mM sodium ortho-vanadate, 10 µM adenosine-tri-phosphate (ATP), 0.5 µM substrate, 0.001% (v/v) Nonidet-P40 (Sigma), 1% (v/v) dimethylsulfoxide]. The concentration of VEGFR2 was adjusted depending of the activity of the enzyme lot and was chosen appropriate to have the assay in the linear range. The reaction was stopped by the addition of 5 µl of a solution of HTRF detection reagents (0.1 µM streptavidine-XLent and 2 nM PT66-Eu-Chelate, an europium-chelate labelled anti-phospho-tyrosine antibody from Perkin Elmer) in an aqueous EDTA-solution (125 mM EDTA, 0.2% (w/v) bovine serum albumin in 50 mM HEPES/NaOH pH 7.0).

The resulting mixture was incubated for 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalized (enzyme reaction without inhibitor=0% inhibition, all other assay components but no enzyme=100% inhibition) and $IC_{50}$ values were calculated by a 4 parameter fit using an inhouse software.

Assay 6: PDGFRβ HTRF Assay

PDGFRβ inhibitory activity of compounds of the present invention was quantified employing the PDGFRβ HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] was used. As substrate for the kinase reaction the biotinylated poly-Glu, Tyr (4:1) copolymer (#61GT0BLA) from Cis Biointernational (Marcoule, France) was used.

For the assay 50 nl of a 100 fold concentrated solution of the test compound in DMSO was pipetted into a black low volume 384 well microtiter plate (Greiner Bio-One, Frickenhausen, Germany), 2 μl of a solution of PDGFRβ in aqueous assay buffer [50 mM HEPES/NaOH pH 7.5, 10 mM $MgCl_2$, 2.5 mM dithiothreitol, 0.01% (v/v) Triton-X100 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (2.27 μg/ml=>final conc. in the 5 μl assay volume is 1.36 μg/ml [~30 nM]) in assay buffer and the resulting mixture was incubated for a reaction time of 25 min at 22° C. The concentration of PDG-FRβ in the assay was adjusted depending of the activity of the enzyme lot and was chosen appropriate to have the assay in the linear range, typical enzyme concentrations were in the range of about 125 pg/μl (final conc. in the 5 μl assay volume). The reaction was stopped by the addition of 5 μl of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer) in an aqueous EDTA-solution (100 mM EDTA, 0.2% (w/v) bovine serum albumin in 50 mM HEPES/NaOH pH 7.5).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Assay 7: TrkA HTRF Assay

Trk-A inhibitory activity of compounds of the present invention was quantified employing the Trk-A HTRF assay as described in the following paragraphs.

As kinase, a GST-His fusion protein containing a C-terminal fragment of human Trk-A (amino acids G443-G796, expressed in insect cells [SF9] and purified by affinity chromatography, purchased from Proqinase [Freiburg i.Brsg., Germany] was used. As substrate for the kinase reaction the biotinylated poly-Glu, Tyr (4:1) copolymer (#61GT0BLA) from Cis Biointernational (Marcoule, France) was used. For the assay 50 nl of a 100 fold concentrated solution of the test compound in DMSO was pipetted into a black low volume 384 well microtiter plate (Greiner Bio-One, Frickenhausen, Germany), 2 μl of a solution of TrkA in aqueous assay buffer [8 mM MOPS/NaOH pH 7.0, 10 mM $Mg(OAc)_2$, 1 mM dithiothreitol, 0.01% (v/v) NP-40 (Fluka), 0.2 mM EDTA] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (2.27 μg/ml=>final conc. in the 5 μl assay volume is 1.36 μg/ml [~30 nM]) in assay buffer and the resulting mixture was incubated for a reaction time of 60 min at 22° C. The concentration of Trk-A in the assay was adjusted depending of the activity of the enzyme lot and was chosen appropriate to have the assay in the linear range, typical enzyme concentrations were in the range of about 60 pg/μl (final conc. in the 5 μl assay volume). The reaction was stopped by the addition of 5 μl of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer) in an aqueous EDTA-solution (100 mM EDTA, 0.2% (w/v) bovine serum albumin in 50 mM HEPES/NaOH pH 7.5).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Additional Assays: Upstate KinaseProfiler®—Radio-Enzymatic Filter Binding Assay:

Upstate KinaseProfiler™—Radio-Enzymatic Filter Binding Assay

Compounds of the present invention are assessed for their ability to inhibit individual members of the kinase panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing $MnCl_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Further kinase assay protocols which may be used are given in the document "KinaseProfiler™ Service Assay Protocols", published by Millipore Corporation under http://www.millipore.com/techpublications/tech1/cd1000enus, which is hereby incorporated by reference in its entirety.

Biological Data

Compounds of the present invention were found to possess balanced inhibition of VEGFR2 kinase and PDGFRβ kinase and/or Tie2 kinase with a favourable selectivity profile within the class of tyrosine kinases. Preferred compounds of the present invention show, for example, selectivity against insulin receptor kinase (InsR) and/or the nerve-growth factor receptor TrkA. More preferred compounds of the present invention potently inhibit VEGFR2 and PDGFRβ and Tie2 kinase, while being selective against InsR and TrkA.

Selected data are given in the following table. The $IC_{50}$ values were converted to $pIC_{50}$ values, i.e. $-\log IC_{50}$ in molar concentration.

| Example No. | Enzymatic Tie 2 activity (assay 2) | Enzymatic VEGFR2 activity (assay 5) | Enzymatic PDGFRβ activity (assay 6) | Enzymatic TrkA activity (assay 7) | Enzymatic InsR activity (assay 4) |
|---|---|---|---|---|---|
| 1.5 | + | + | + | -- | -- |
| 1.6 | + | + | + | -- | -- |
| 1.9 | + | + |   | -- | -- |
| 2.1 | + | + | + | -- | -- |
| 2.4 | + | + | + | -- |   |
| 2.6 | + | + |   |   | -- |

-- represents $pIC_{50} \leq 5.0$

– represents $pIC_{50}$ 5.0-6.0

+ represents $pIC_{50} > 6.0$

General Remarks

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. All publications, applications and patents/patent applications cited above are incorporated herein by reference.

The topic headings set forth above and below are meant as guidance where certain information can be found in the application, but are not intended to be the only source in the application where information on such topic can be found.

The invention claimed is:

1. A compound of formula (I):

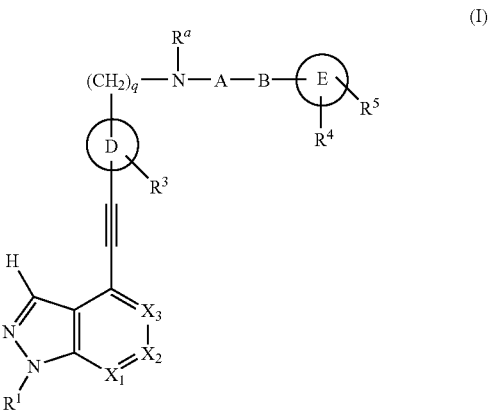

in which:

$R^1$ represents H or —C(O)$R^b$, or is $C_1$-$C_6$-alkyl, $C_2$-$C_6$-alkenyl, $C_2$-$C_6$-alkynyl, $C_3$-$C_{10}$-cycloalkyl, or $C_3$-$C_{10}$-heterocycloalkyl, wherein said residues are unsubstituted or substituted one or more times, independently from each other, with $R^6$;

$R^2$ represents hydrogen, halogen, cyano, —NR$^{d1}$R$^{d2}$, —OR$^c$, —C(O)R$^b$, or is $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, or heteroaryl, wherein said residues are unsubstituted or one or more times substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, or cyano;

$R^4$, $R^5$, $R^6$, $R^7$ independently from each other, are hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or —OP(O)(OR$^c$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;

$R^8$ is $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or —OP(O)(OR$^c$)$_2$;

$R^a$ is hydrogen or $C_1$-$C_6$-alkyl;

$R^b$ is hydroxyl, —OR$^c$, —SR$^c$, —NR$^{d1}$R$^{d2}$, $C_1$-$C_6$-alkyl, or $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^c$ is hydrogen, —C(O)R$^e$, $C_1$-$C_6$-alkyl, $C_1$-$C_6$-haloalkyl $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —OR$^f$, —NR$^{d1}$R$^{d2}$ or —OP(O)(OR$^f$)$_2$;

$R^{d1}$, $R^{d2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl, or for a group —C(O)R$^e$, —S(O)$_2$R$^e$, or —C(O)NR$^{g1}$R$^{g2}$ wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, halogen, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, or —S(O)$_2$— group, and can optionally contain one or more double bonds;

R$^{d3}$ is hydrogen, C$_1$-C$_6$-alkyl, C$_3$-C$_{10}$-cycloalkyl, C$_3$-C$_{10}$-heterocycloalkyl, aryl, or heteroaryl, wherein C$_1$-C$_6$-alkyl, and C$_3$-C$_{10}$-cycloalkyl are optionally substituted one or more times with C$_1$-C$_6$-alkyl, C$_3$-C$_{10}$-cycloalkyl, hydroxyl, halogen, C$_1$-C$_6$-haloalkyl or C$_1$-C$_6$-alkoxy;

R$^e$ is —NR$^{g1}$R$^{g2}$, C$_1$-C$_6$-alkyl, C$_3$-C$_6$-cycloalkyl, C$_1$-C$_6$-alkoxy, aryl or heteroaryl;

R$^f$ is s hydrogen, —C(O)R$^e$, C$_1$-C$_6$-alkyl, C$_1$-C$_6$-haloalkyl, C$_3$-C$_{10}$-cycloalkyl, C$_3$-C$_{10}$-heterocycloalkyl, aryl, or heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, C$_1$-C$_6$-alkoxy, aryl, or —NR$^{g1}$R$^{g2}$;

R$^{g1}$, R$^{g2}$ independently from each other are hydrogen, C$_1$-C$_6$-alkyl, C$_3$-C$_{10}$-cycloalkyl, C$_3$-C$_{10}$-heterocycloalkyl, aryl, or heteroaryl;

R$^{g1}$ and R$^{g2}$ together with the nitrogen atom to which they are attached, form a 3 to 10 membered heterocycloalkyl ring, which is optionally substituted one or more times, the same way or differently, with C$_1$-C$_6$-alkyl, —C$_1$-C$_6$-alkoxy, halogen or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, or —S(O)$_2$— group, and can optionally contain one or more double bonds;

A is —C(O)—, —C(S)—, —C(=NR$^a$)—, —C(O)NR$^a$—, —C(=NR$^a$)NR$^a$—, —S(O)$_2$—, —S(O)(=NR$^a$)—, —S(=NR$^a$)$_2$—, —C(S)NR$^a$—, —C(O)C(O)—, —C(O)C(O)NR$^a$—, —C(O)NR$^a$C(O)—, —C(S)NR$^a$C(O)—, or —C(O)NR$^a$C(S)—;

B is a bond C$_1$-C$_6$-alkylene, C$_3$-C$_{10}$-cycloalkylene, or C$_3$-C$_{10}$-heterocycloalkylene;

D is arylene;

E is arylene or heteroarylene;

X$_1$ and X$_3$ are CH;

X$_2$ is N;

and q represents an integer of 0, 1, or 2;

or a salt thereof, wherein two or more occurrences of R$^a$, R$^b$, R$^c$, R$^{d1}$, R$^{d2}$, R$^{d3}$, R$^e$, R$^f$, R$^{g1}$, R$^{g2}$, or R$^8$ within a single molecule may be identical or different.

2. The compound according to claim 1, wherein:

R$^1$ represents H or —C(O)R$^b$, or is C$_1$-C$_6$-alkyl, C$_2$-C$_6$-alkenyl, C$_2$-C$_6$-alkynyl, C$_3$-C$_{10}$-cycloalkyl, or C$_3$-C$_{10}$-heterocycloalkyl, wherein said residues are unsubstituted or substituted one or more times, independently from each other, with R$^6$;

R$^2$ represents hydrogen, halogen, cyano, NR$^{d1}$R$^{d2}$, —OR$^c$, —C(O)R$^b$, or is C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, aryl, or heteroaryl, wherein said residues are unsubstituted or one or more times substituted independently from each other with R$^7$;

R$^3$ is hydrogen, C$_1$-C$_6$-alkyl, C$_1$-C$_6$-alkoxy, C$_1$-C$_6$-haloalkyl, C$_1$-C$_6$-haloalkoxy, hydroxy, amino, halogen, or cyano;

R$^4$, R$^5$, R$^6$, R$^7$ independently from each other, are hydrogen, C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or OP(O)(OR$^c$)$_2$, wherein C$_1$-C$_6$-alkyl, aryl, heteroaryl, C$_3$-C$_{10}$-heterocycloalkyl and C$_3$-C$_{10}$-cycloalkyl are optionally substituted one or more times by R$^8$;

R$^8$ is C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or —OP(O)(OR$^c$)$_2$;

R$^a$ is hydrogen or C$_1$-C$_6$-alkyl;

R$^b$ is hydroxyl, —OR$^c$, —SR$^c$, —NR$^{d1}$R$^{d2}$, C$_1$-C$_6$-alkyl, or C$_3$-C$_{10}$-cycloalkyl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^c$ is hydrogen, —C(O)R$^e$, C$_1$-C$_6$-alkyl, C$_1$-C$_6$-haloalkyl C$_3$-C$_{10}$-cycloalkyl, C$_3$-C$_{10}$-heterocycloalkyl, aryl, or heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, aryl, —OR$^f$, —NR$^{d1}$R$^{d2}$, or —OP(O)(OR$^f$)$_2$;

R$^{d1}$, R$^{d2}$ independently from each other are hydrogen, C$_1$-C$_6$-alkyl, C$_3$-C$_{10}$-cycloalkyl, C$_3$-C$_{10}$-heterocycloalkyl, aryl, or heteroaryl, or for a group —C(O)R$^e$, —S(O)$_2$R$^e$, or —C(O)NR$^{g1}$R$^{g2}$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, halogen, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, or —S(O)$_2$— group, and can optionally contain one or more double bonds R$^{d3}$ is hydrogen, C$_1$-C$_6$-alkyl, C$_3$-C$_{10}$-cycloalkyl, C$_3$-C$_{10}$-heterocycloalkyl, aryl, or heteroaryl, wherein C$_1$-C$_6$-alkyl, and C$_3$-C$_{10}$-cycloalkyl are optionally substituted one or more times with C$_1$-C$_6$-alkyl, C$_3$-C$_{10}$-cycloalkyl, hydroxyl, halogen, C$_1$-C$_6$-haloalkyl or C$_1$-C$_6$-alkoxy;

R$^e$ is —NR$^{g1}$R$^{g2}$, C$_1$-C$_6$-alkyl, C$_3$-C$_6$-cycloalkyl, C$_1$-C$_6$-alkoxy, aryl or heteroaryl;

$R^f$ is hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —NR$^{g1}$R$^{g2}$;

$R^{g1}$, $R^{g2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, or —S(O)$_2$— group, and can optionally contain one or more double bonds;

A is —C(O)—, or —C(O)NR$^a$—;
B is a bond or $C_1$-$C_3$-alkylene, or $C_3$-$C_6$-cycloalkylene;
D is arylene;
E is arylene or heteroarylene;
$X_1$ and $X_3$ are CH;
$X_2$ is N;
and
q represents an integer of 0, 1, or 2.

3. The compound according to claim 1, wherein:
$R^1$ represents H or —C(O)$R^b$, or is $C_1$-$C_6$-alkyl, $C_2$-$C_6$-alkenyl, $C_2$-$C_6$-alkynyl, $C_3$-$C_{10}$-cycloalkyl, or $C_3$-$C_{10}$-heterocycloalkyl, wherein said residues are unsubstituted or substituted one or more times, independently from each other, with $R^6$;

$R^2$ represents hydrogen, halogen, cyano, NR$^{d1}$R$^{d2}$, —OR$^c$, —C(O)$R^b$, or is $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, or heteroaryl, wherein said residues are unsubstituted or one or more times substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, or cyano;

$R^4$, $R^5$, $R^6$, $R^7$ independently from each other, are hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, —NR$^{d1}$R$^{d2}$, or —OP(O)(OR$^c$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;

$R^8$ is $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, —NR$^{d1}$R$^{d2}$, or —OP(O)(OR$^c$)$_2$;

$R^a$ is hydrogen or $C_1$-$C_6$-alkyl;
$R^b$ is hydroxyl, —OR$^c$, —SR$^c$, —NR$^{d1}$R$^{d2}$, $C_1$-$C_6$-alkyl, or $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^c$ is hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —OR$^f$, —NR$^{d1}$R$^{d2}$, or —OP(O)(OR$^f$)$_2$;

$R^{d1}$, $R^{d2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl, or for a group —C(O)$R^e$, —S(O)$_2$$R^e$, or —C(O)NR$^{g1}$R$^{g2}$, wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)$R^e$, —S(O)$_2$$R^e$, or —OP(O)(OR$^f$)$_2$; or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, halogen, —NR$^{g1}$R$^{g2}$, —OR$^f$, —C(O)$R^e$, —S(O)$_2$$R^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, or —S(O)$_2$— group, and can optionally contain one or more double bonds $R^{d3}$ is hydrogen, $C_1$-$C_6$-alkyl, $C_3$-$C_{10}$-cycloalkyl, $C_3$-$C_{10}$-heterocycloalkyl, aryl, or heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;

$R^e$ is —NR$^{g1}$R$^{g2}$, $C_1$-$C_6$-alkyl, $C_3$-$C_6$-cycloalkyl, $C_1$-$C_6$-alkoxy, aryl or heteroaryl;

$R^f$ is hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —NR$^{g1}$R$^{g2}$;

$R^{g1}$, $R^{g2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, or —S(O)$_2$— group, and can optionally contain one or more double bonds;

A is —C(O)— or —C(O)NR$^a$—;
B is a bond, $C_1$-$C_3$-alkylene, or $C_3$-$C_6$-cycloalkylene;
D is phenylene;
E is arylene or heteroarylene;
$X_1$ and $X_3$ are CH;
$X_2$ is N,
and
q represents an integer of 0, 1, or 2.

4. The compound according to claim 1, wherein:
$R^1$ represents $C_1$-$C_6$-alkyl;
$R^3$ is hydrogen, $C_1$-$C_6$-alkyl, or halogen;

$R^4$, $R^5$ independently from each other, are hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, —NR$^{d1}$R$^{d2}$, or —OP(O)(OR$^c$)$_2$, wherein $C_1$-$C_6$-alkyl, aryl, heteroaryl, $C_3$-$C_{10}$-heterocycloalkyl and $C_3$-$C_{10}$-cycloalkyl are optionally substituted one or more times by $R^8$;

$R^8$ is $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$$R^b$, —OR$^c$, —NR$^{d1}$R$^{d2}$, or —OP(O)(OR$^c$)$_2$;

$R^a$ is hydrogen;

$R^b$ is hydroxyl, —OR$^c$, —SR$^c$, —NR$^{d1}$R$^{d2}$, $C_1$-$C_6$-alkyl, or $C_3$-$C_{10}$-cycloalkyl, wherein $C_1$-$C_6$-alkyl, and $C_3$-$C_{10}$-cycloalkyl are optionally substituted one or more times with hydroxyl, halogen, or $C_1$-$C_6$-alkoxy;

$R^c$ is hydrogen, —C(O)$R^e$, $C_1$-$C_6$-alkyl, $C_1$-$C_6$-haloalkyl $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, aryl, —OR$^f$, —NR$^{d1}$R$^{d2}$, or —OP(O)(OR$^f$)$_2$;

$R^{d1}$, $R^{d2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl, or for a group —C(O)$R^e$, —S(O)$_2$$R^e$, or —C(O)NR$^{g1}$R$^{g2}$, wherein $C_1$-$C_6$-alkyl, $C_3$-$C_{10}$-cycloalkyl, $C_3$-$C_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)$R^e$, —S(O)$_2$$R^e$, or —OP(O)(OR$^f$)$_2$, or $R^{d1}$ and $R^{d2}$ together with the nitrogen atom to which they are attached, form a 3 to 10 membered heterocycloalkyl ring, which is optionally substituted one or more times, the same way or differently, with $C_1$-$C_6$-alkyl, halogen, —NR$^{g1}$R$^{g2}$, —OR$^f$, —C(O)$R^e$, —S(O)$_2$$R^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, or —S(O)$_2$— group, and can optionally contain one or more double bonds;

$R^{d3}$ is hydrogen, $C_1$-$C_6$-alkyl, $C_3$-$C_{10}$-cycloalkyl, $C_3$-$C_{10}$-heterocycloalkyl, aryl, or heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;

$R^e$ is —NR$^{g1}$R$^{g2}$, $C_1$-$C_6$-alkyl, $C_3$-$C_6$-cycloalkyl, $C_1$-$C_6$-alkoxy, aryl, or heteroaryl;

$R^f$ is hydrogen, —C(O)$R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, or heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —NR$^{g1}$R$^{g2}$;

$R^{g1}$, $R^{g2}$ independently from each other are hydrogen, $C_1$-$C_6$-alkyl, $C_3$-$C_{10}$-cycloalkyl, $C_3$-$C_{10}$-heterocycloalkyl, aryl, or heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, NR$^a$, oxygen or sulphur, and can optionally be interrupted one or more times, the same way or differently, with a —C(O)—, —S(O)—, or —S(O)$_2$— group, and can optionally contain one or more double bonds;

A is —C(O)— or —C(O)NR$^a$—;

B is a bond, $C_1$-$C_3$-alkylene, or $C_3$-$C_6$-cycloalkylene;

D is phenylene;

E is arylene or heteroarylene;

$X_1$ is a CH group;

$X_2$ is a nitrogen atom;

$X_3$ is a CH group; and q represents an integer of 0, 1, or 2.

5. The compound according to claim 1 selected from the group consisting of:

N-[3-(1-Methyl-1H-pyrazolo[3,4-c]pyridin-4-ylethynyl)-phenyl]-benzamide;

N-[4-Methyl-3-(1-methyl-1H-pyrazolo[3,4-c]pyridin-4-ylethynyl)-phenyl]-benzamide;

2,4-Dichloro-N-[3-(1-methyl-1H-pyrazolo[3,4-c]pyridin-4-ylethynyl)-phenyl]-benzamide;

2,4-Dichloro-N-[4-methyl-3-(1-methyl-1H-pyrazolo[3,4-c]pyridin-4-ylethynyl)-phenyl]-benzamide;

N-[3-(1-Methyl-1H-pyrazolo[3,4-c]pyridin-4-ylethynyl)-phenyl]-3-trifluoromethyl-benzamide;

N-[4-Methyl-3-(1-methyl-1H-pyrazolo[3,4-c]pyridin-4-ylethynyl)-phenyl]-3-trifluoromethyl-benzamide;

2-Fluoro-5-methyl-N-[3-(1-methyl-1H-pyrazolo[3,4-c]pyridin-4-ylethynyl)-phenyl]-benzamide;

2-Fluoro-5-methyl-N-[4-methyl-3-(1-methyl-1H-pyrazolo[3,4-c]pyridin-4-ylethynyl)-phenyl]-benzamide;

1-[3-(1-Methyl-1H-pyrazolo[3,4-c]pyridin-4-ylethynyl)-phenyl]-3-phenyl-urea;

1-[4-Methyl-3-(1-methyl-1H-pyrazolo[3,4-c]pyridin-4-ylethynyl)-phenyl]-3-phenyl-urea;

1-[3-(1-Methyl-1H-pyrazolo[3,4-c]pyridin-4-ylethynyl)-phenyl]-3-(3-trifluoromethyl-phenyl)-urea;

1-[4-Methyl-3-(1-methyl-1H-pyrazolo[3,4-c]pyridin-4-ylethynyl)-phenyl]-3-(3-trifluoromethyl-phenyl)-urea;

1-(2-Fluoro-5-methyl-phenyl)-3-[3-(1-methyl-1H-pyrazolo[3,4-c]pyridin-4-ylethynyl)-phenyl]-urea;

1-[2-(3-Fluoro-phenyl)-5-isopropyl-2H-pyrazol-3-yl]-3-[3-(1-methyl-1H-pyrazolo[3,4-c]pyridin-4-ylethynyl)-phenyl]-urea;

1-[5-Isopropyl-2-(3-methoxy-phenyl)-2H-pyrazol-3-yl]-3-[3-(1-methyl-1H-pyrazolo[3,4-c]pyridin-4-ylethynyl)-phenyl]-urea;

N-[4-Fluoro-3-(1-methyl-1H-pyrazolo[3,4-c]pyridin-4-ylethynyl)-phenyl]-3-trifluoromethyl-benzamide;

1-[4-Fluoro-3-(1-methyl-1H-pyrazolo[3,4-c]pyridin-4-ylethynyl)-phenyl]-3-(3-trifluoromethyl-phenyl)-urea; and 1-[4-(4-Methyl-piperazin-1-ylmethyl)-3-trifluoromethyl-phenyl]-3-[3-(1-methyl-1H-pyrazolo[3,4-c]pyridin-4-ylethynyl)-phenyl]-urea.

6. A method of preparing a compound of formula (I) according to claim 1, said method comprising the step of reacting an intermediate compound of general formula 1:

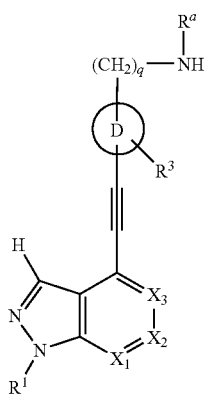

in which D, R$^a$, R$^1$, R$^3$, X$_1$, X$_2$, X$_3$ and q are as defined claim 1, with an electrophile, a suitably functionalized sulfonyl chloride, a suitably functionalized acid chloride, or a suitably functionalized carboxylic acid, optionally in the presence of a coupling agent, and optionally in the presence of a suitable base, thereby giving a compound of formula I:

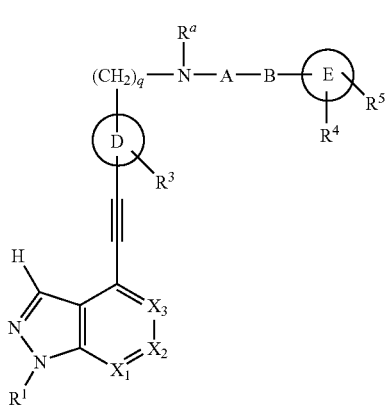

(I)

in which A, B, D, E, R$^a$, R$^1$, R$^3$, R$^4$, R$^5$, X$_1$, X$_2$, X$_3$ and q are as defined in claim 1.

7. A method of preparing a compound of formula (Ia):

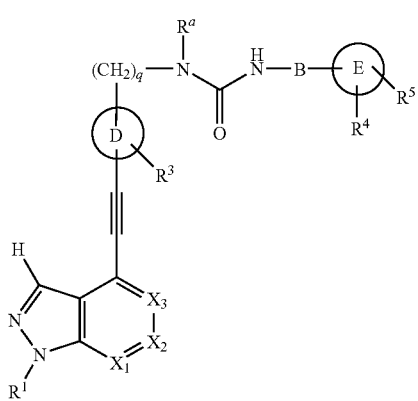

Ia in which

R$^1$ represents H or —C(O)R$^b$, or is C$_1$-C$_6$-alkyl, C$_2$-C$_6$-alkenyl, C$_2$-C$_6$-alkynyl, C$_3$-C$_{10}$-cycloalkyl, or C$_3$-C$_{10}$-heterocycloalkyl, wherein said residues are unsubstituted or substituted one or more times, independently from each other, with R$^6$;

R$^2$ represents hydrogen, halogen, cyano, —NR$^{d1}$R$^{d2}$, —OR$^c$, —C(O)R$^b$, or is C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, aryl, or heteroaryl, wherein said residues are unsubstituted or one or more times substituted independently from each other with R$^7$;

R$^3$ is hydrogen, C$_1$-C$_6$-alkyl, C$_1$-C$_6$-alkoxy, C$_1$-C$_6$-haloalkyl, C$_1$-C$_6$-haloalkoxy, hydroxy, amino, halogen, or cyano;

R$^4$, R$^5$, R$^6$, R$^7$ independently from each other, are hydrogen, C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or OP(O)(OR$^c$)$_2$, wherein C$_1$-C$_6$-alkyl, aryl, heteroaryl, C$_3$-C$_{10}$-heterocycloalkyl, and C$_3$-C$_{10}$-cycloalkyl are optionally substituted one or more times by R$^8$;

R$^8$ is C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, or —OP(O)(OR$^c$)$_2$;

R$^a$ is hydrogen and C$_1$-C$_6$-alkyl;

R$^b$ is hydroxyl, —OR$^c$, —NR$^{d1}$R$^{d2}$, C$_1$-C$_6$-alkyl, and C$_3$-C$_{10}$-cycloalkyl, wherein C$_1$-C$_6$-alkyl, and C$_3$-C$_{10}$-cycloalkyl are optionally substituted one or more times with hydroxyl, halogen, or C$_1$-C$_6$-alkoxy;

R$^c$ is hydrogen, —C(O)R$^e$, C$_1$-C$_6$-alkyl, C$_1$-C$_6$-haloalkyl C$_3$-C$_{10}$-cycloalkyl, C$_3$-C$_{10}$-heterocycloalkyl, aryl, or heteroaryl, wherein C$_1$-C$_6$-alkyl, C$_1$-C$_6$-haloalkyl, C$_3$-C$_{10}$-cycloalkyl, C$_3$-C$_{10}$-heterocycloalkyl, aryl, and heteroaryl are optionally substituted one or more times with hydroxyl, halogen, aryl, —OR$^f$, —NR$^{d1}$R$^{d2}$ or —OP(O)(OR$^f$)$_2$;

R$^{d1}$, R$^{d2}$ independently from each other are hydrogen, C$_1$-C$_6$-alkyl, C$_3$-C$_{10}$-cycloalkyl, C$_3$-C$_{10}$-heterocycloalkyl, aryl, and heteroaryl, or for a group —C(O)R$^e$, —S(O)$_2$R$^e$, or —C(O)NR$^{g1}$R$^{g2}$ wherein C$_1$-C$_6$-alkyl, C$_3$-C$_{10}$-cycloalkyl, C$_3$-C$_{10}$-heterocycloalkyl, aryl, and heteroaryl are optionally substituted one or more times, the same way or differently with halogen, hydroxy or the group aryl, —NR$^{g1}$R$^{g2}$, —OR$^f$, —C(O)R$^e$, —S(O)$_2$R$^e$, or —OP(O)(OR$^f$)$_2$; or R$^{d1}$ and R$^{d2}$ together with the nitrogen atom to which they are attached, form a 3 to 10 membered heterocycloalkyl ring, which is optionally substituted one or more times, the same way or differently, with C$_1$-C$_6$-alkyl, halogen, —NR$^{g1}$R$^{g2}$, —OR$^f$, —C(O)R$^e$, —S(O)$_2$R$^e$, or —OP(O)(OR$^f$)$_2$; whereby the carbon backbone of this heterocycloalkyl ring can optionally be interrupted one or more times, the same way or differently, by a member of the group comprising, preferably consisting of, NH, NR$^{d3}$, oxygen or sulphur, and can optionally be interrupted one or more times, the same way or differently, with a —C(O)—, —S(O)—, or —S(O)$_2$— group, and can optionally contain one or more double bonds $R^{d3}$ is hydrogen, $C_1$-$C_6$-alkyl, $C_3$-$C_{10}$-cycloalkyl, $C_3$-$C_{10}$-heterocycloalkyl, aryl, and heteroaryl, wherein $C_1$-$C_6$-alkyl, and $C_3$-$C_{10}$-cycloalkyl are optionally substituted one or more times with $C_1$-$C_6$-alkyl, $C_3$-$C_{10}$-cycloalkyl, hydroxyl, halogen, $C_1$-$C_6$-haloalkyl or $C_1$-$C_6$-alkoxy;

$R^e$ is —$NR^{g1}R^{g2}$, $C_1$-$C_6$-alkyl, $C_3$-$C_6$-cycloalkyl, $C_1$-$C_6$-alkoxy, aryl and heteroaryl;

$R^f$ is hydrogen, —$C(O)R^e$, $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl, wherein $C_1$-$C_6$-alkyl, $C_1$-$C_6$-haloalkyl, $C_3$-$C_{10}$-cycloalkyl, $C_3$-$C_{10}$-heterocycloalkyl, aryl, and heteroaryl are optionally substituted one or more times with hydroxyl, halogen, $C_1$-$C_6$-alkoxy, aryl, or —$NR^{g1}R^{g2}$;

$R^{g1}$, $R^{g2}$ independently from each other are hydrogen, $C_1$-$C_6$-alkyl, $C_3$-$C_{10}$-cycloalkyl, $C_3$-$C_{10}$-heterocycloalkyl, aryl, and heteroaryl;

$R^{g1}$ and $R^{g2}$ together with the nitrogen atom to which they are attached, form a 3 to 10 membered heterocycloalkyl ring, which is optionally substituted one or more times, the same way or differently, with $C_1$-$C_6$-alkyl, —$C_1$-$C_6$-alkoxy, halogen or hydroxy; whereby the carbon backbone of this heterocycloalkyl ring can optionally be interrupted one or more times, the same way or differently, by a member of the group comprising, preferably consisting of, NH, $NR^a$, oxygen or sulphur, and can optionally be interrupted one or more times, the same way or differently, with a —C(O)—, —S(O)—, or —$S(O)_2$— group, and can optionally contain one or more double bonds;

B is a bond or $C_1$-$C_6$-alkylene, $C_3$-$C_{10}$-cycloalkylene, and $C_3$-$C_{10}$-heterocycloalkylene;

D is arylene;

E is arylene or heteroarylene;

$X_1$ and $X_3$ are CH;

$X_2$ is N;

and q represents an integer of 0, 1, or 2, said method comprising the step of reacting an intermediate compound of general formula 1 or 3 or 5:

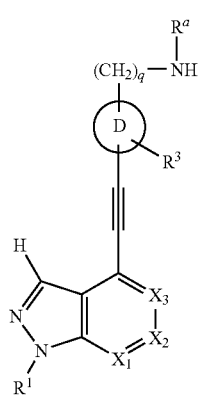

1

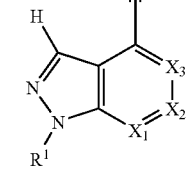

3

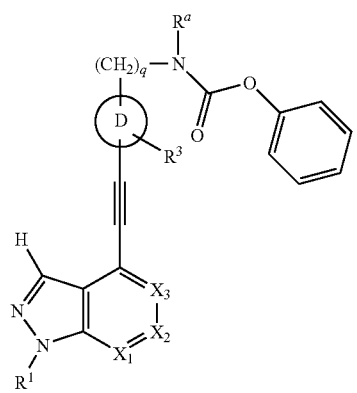

5 in which D, $R^a$, $R^1$, $R^3$, $X_1$, $X_2$, $X_3$ and q are as defined in this claim, with a (hetero)aryl amine of general formula 2:

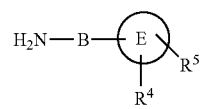

2 in which B, E, $R^4$, and $R^5$, are as defined in this claim,
optionally in the presence of a carbonylating agent,
thereby giving a compound of above-mentioned formula Ia.

8. A method of preparing a compound of formula (I) according to claim 1, said method comprising the step of reacting an intermediate compound of general formula 15:

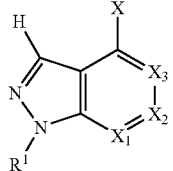

15 in which $R^1$, $X_1$, $X_2$, and $X_3$ are as defined in claim 1, and X represents a halogen atom, by a coupling reaction with a compound of general formula 19:

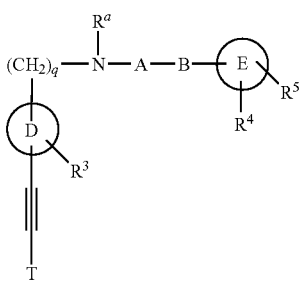

19 in which D, $R^a$, $R^3$, $R^4$, $R^5$ and q are as defined in claim 1, and T represents a hydrogen atom or a trialkylsilyl group, thereby giving a compound of formula (I):

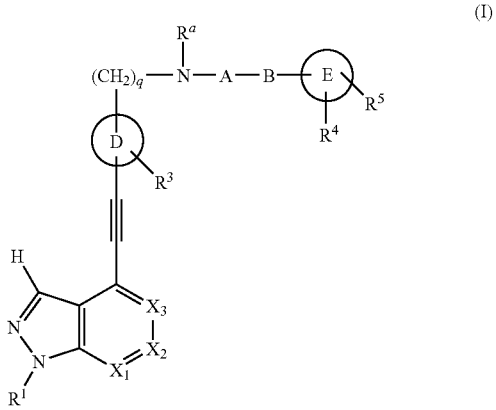

(I)

in which A, B, D, E, $R^a$, $R^1$, $R^3$, $R^4$, $R^5$, $X_1$, $X_2$, $X_3$ and q are as defined in claim 1.

9. A pharmaceutical composition comprising a compound of general formula (I) according to claim 1 or a pharmaceutically acceptable salt thereof and a pharmaceutically acceptable diluent or carrier.

\* \* \* \* \*